US007892203B2

(12) United States Patent
Lenker et al.

(10) Patent No.: US 7,892,203 B2
(45) Date of Patent: Feb. 22, 2011

(54) EXPANDABLE TRANSLUMINAL SHEATH

(75) Inventors: Jay Lenker, Laguna Beach, CA (US);
Edward J. Nance, Corona, CA (US);
Joseph Bishop, Menifee, CA (US);
George F. Kick, Casa Grande, AZ (US)

(73) Assignee: Onset Medical Corporation, Irvine, CA (US)

( * ) Notice: Subject to any disclaimer, the term of this patent is extended or adjusted under 35 U.S.C. 154(b) by 1340 days.

(21) Appl. No.: 11/199,566

(22) Filed: Aug. 8, 2005

(65) Prior Publication Data

US 2006/0052750 A1  Mar. 9, 2006

Related U.S. Application Data

(60) Provisional application No. 60/660,512, filed on Mar. 9, 2005, provisional application No. 60/608,355, filed on Sep. 9, 2004.

(51) Int. Cl.
*A61M 31/00* (2006.01)
(52) U.S. Cl. .................................. 604/103.05
(58) Field of Classification Search ............... 604/96.01, 604/164.01–164.03, 523–527, 103.5; 606/191–194
See application file for complete search history.

(56) References Cited

U.S. PATENT DOCUMENTS

| | | | |
|---|---|---|---|
| 319,296 A | 6/1885 | Molesworth |
| 668,879 A | 2/1901 | Miller |
| 1,213,001 A | 1/1917 | Philips |
| 1,248,492 A | 12/1917 | Hill |
| 2,042,900 A | 6/1936 | James |
| 2,548,602 A | 4/1948 | Greenburg |
| 3,509,883 A | 5/1970 | Dibelius |
| 3,545,443 A | 12/1970 | Ansari |
| 3,742,958 A | 7/1973 | Rundles |
| 3,789,852 A | 2/1974 | Kim et al. |
| 3,902,492 A | 9/1975 | Greenhalgh |
| 4,018,230 A | 4/1977 | Ochiai et al. |
| 4,141,364 A | 2/1979 | Schultze |
| 4,338,942 A | 7/1982 | Fogarty |

(Continued)

FOREIGN PATENT DOCUMENTS

EP   0177177   4/1986

(Continued)

OTHER PUBLICATIONS

Jul. 14, 2008 European Patent Office Communication in Euro. App. No. 05 794 899.4 filed on Sep. 8, 2005.

(Continued)

*Primary Examiner*—Manual A Mendez
(74) *Attorney, Agent, or Firm*—Knobbe, Martens, Olson & Bear, LLP.

(57) ABSTRACT

Disclosed is an expandable transluminal sheath, for introduction into the body while in a first, low cross-sectional area configuration, and subsequent expansion of at least a part of the distal end of the sheath to a second, enlarged cross-sectional configuration. The distal end of the sheath is maintained in the first, low cross-sectional configuration and expanded using a radial dilatation device. In an exemplary application, the sheath is utilized to provide access for a diagnostic or therapeutic procedure such as ureteroscopy or stone removal.

24 Claims, 14 Drawing Sheets

U.S. PATENT DOCUMENTS

| | | |
|---|---|---|
| 4,401,433 A | 8/1983 | Luther |
| 4,411,655 A | 10/1983 | Schreck |
| 4,451,256 A | 5/1984 | Weikl et al. |
| 4,479,497 A | 10/1984 | Fogarty et al. |
| 4,581,025 A | 4/1986 | Timmermans |
| 4,589,868 A | 5/1986 | Dretler |
| 4,601,713 A | 7/1986 | Fuqua |
| 4,610,688 A | 9/1986 | Silvestrini et al. |
| 4,636,346 A * | 1/1987 | Gold et al. .................. 264/139 |
| 4,650,466 A | 3/1987 | Luther |
| 4,710,181 A | 12/1987 | Fuqua |
| 4,716,901 A | 1/1988 | Jackson et al. |
| 4,738,666 A | 4/1988 | Fuqua |
| 4,739,762 A | 4/1988 | Palmaz |
| 4,772,266 A | 9/1988 | Groshong |
| 4,790,817 A | 12/1988 | Luther |
| 4,798,193 A | 1/1989 | Giesy et al. |
| 4,846,791 A | 7/1989 | Hattler et al. |
| 4,865,593 A | 9/1989 | Ogawa et al. |
| 4,869,717 A | 9/1989 | Adair |
| 4,884,573 A | 12/1989 | Wijay et al. |
| 4,888,000 A | 12/1989 | McQuilkin et al. |
| 4,896,669 A | 1/1990 | Bhate et al. |
| 4,898,591 A | 2/1990 | Jang et al. |
| 4,899,729 A | 2/1990 | Gill et al. |
| 4,921,479 A | 5/1990 | Grayzel |
| 4,954,126 A | 9/1990 | Wallsten |
| 4,955,895 A | 9/1990 | Sugiyama et al. |
| 4,972,827 A | 11/1990 | Kishi et al. |
| 4,984,564 A | 1/1991 | Yuen |
| 4,986,830 A | 1/1991 | Owens et al. |
| 5,011,488 A | 4/1991 | Ginsburg et al. |
| 5,035,686 A | 7/1991 | Crittenden et al. |
| 5,045,056 A | 9/1991 | Behl |
| 5,057,092 A | 10/1991 | Webster, Jr. |
| 5,059,183 A | 10/1991 | Semrad |
| 5,066,285 A | 11/1991 | Lundquist et al. |
| 5,073,166 A | 12/1991 | Parks et al. |
| 5,078,736 A | 1/1992 | Behl |
| 5,092,839 A | 3/1992 | Kipperman |
| 5,098,393 A | 3/1992 | Amplatz et al. |
| 5,100,388 A | 3/1992 | Behl et al. |
| 5,108,413 A | 4/1992 | Moyers |
| 5,108,416 A | 4/1992 | Ryan et al. |
| 5,112,304 A | 5/1992 | Barlow et al. |
| 5,112,308 A | 5/1992 | Olsen et al. |
| 5,116,318 A | 5/1992 | Hillstead |
| 5,122,122 A | 6/1992 | Allgood |
| 5,139,511 A | 8/1992 | Gill et al. |
| 5,147,316 A * | 9/1992 | Castillenti .............. 604/164.04 |
| 5,158,545 A | 10/1992 | Trudell et al. |
| 5,163,903 A | 11/1992 | Crittenden et al. |
| 5,176,659 A | 1/1993 | Mancini |
| 5,183,464 A | 2/1993 | Dubrul et al. |
| 5,188,602 A | 2/1993 | Nichols |
| 5,201,756 A | 4/1993 | Horzewski et al. |
| 5,222,938 A | 6/1993 | Behl |
| 5,222,971 A | 6/1993 | Willard et al. |
| 5,234,425 A | 8/1993 | Fogarty et al. |
| 5,250,025 A | 10/1993 | Sosnowski et al. |
| 5,250,033 A | 10/1993 | Evans et al. |
| 5,256,150 A | 10/1993 | Quiachon et al. |
| 5,275,611 A | 1/1994 | Behl |
| 5,279,553 A | 1/1994 | Winkler et al. |
| 5,295,994 A | 3/1994 | Bonutti |
| 5,312,360 A | 5/1994 | Behl |
| 5,312,417 A | 5/1994 | Wilk |
| 5,316,360 A | 5/1994 | Feikema |
| 5,318,588 A | 6/1994 | Horzewski et al. |
| 5,320,611 A | 6/1994 | Bonutti et al. |
| 5,324,261 A | 6/1994 | Amundson et al. |
| 5,346,503 A | 9/1994 | Chow et al. |
| 5,380,304 A | 1/1995 | Parker |
| 5,392,766 A | 2/1995 | Masterson et al. |
| 5,395,341 A | 3/1995 | Slater |
| 5,395,349 A | 3/1995 | Quiachon et al. |
| 5,407,430 A | 4/1995 | Peters |
| 5,409,469 A | 4/1995 | Schaerf |
| 5,431,676 A | 7/1995 | Dubrul et al. |
| 5,433,708 A | 7/1995 | Nichols et al. |
| 5,447,503 A | 9/1995 | Miller |
| 5,454,790 A | 10/1995 | Dubrul |
| 5,460,170 A | 10/1995 | Hammerslag |
| 5,507,767 A | 4/1996 | Maeda et al. |
| 5,514,091 A | 5/1996 | Yoon |
| 5,514,236 A | 5/1996 | Avellanet et al. |
| 5,527,336 A | 6/1996 | Rosenbluth et al. |
| 5,540,658 A | 7/1996 | Evans et al. |
| 5,542,928 A | 8/1996 | Evans et al. |
| 5,549,635 A | 8/1996 | Solar |
| 5,571,089 A | 11/1996 | Crocker |
| 5,573,517 A | 11/1996 | Bonutti et al. |
| 5,573,520 A | 11/1996 | Schwartz |
| 5,657,963 A | 8/1997 | Hincliffe et al. |
| 5,662,614 A | 9/1997 | Edoga |
| 5,672,158 A | 9/1997 | Okada et al. |
| 5,674,240 A | 10/1997 | Bonuttie et al. |
| 5,674,590 A | 10/1997 | Anderson et al. |
| 5,700,253 A | 12/1997 | Parker |
| 5,702,373 A * | 12/1997 | Samson ...................... 604/527 |
| 5,709,713 A | 1/1998 | Evans et al. |
| 5,713,867 A | 2/1998 | Morris |
| 5,738,667 A | 4/1998 | Solar |
| 5,766,203 A | 6/1998 | Imran et al. |
| 5,776,141 A | 7/1998 | Klein et al. |
| 5,810,776 A | 9/1998 | Bacich et al. |
| 5,817,100 A | 10/1998 | Igaki |
| 5,846,251 A | 12/1998 | Hart |
| 5,868,719 A | 2/1999 | Tsukernik |
| 5,868,779 A | 2/1999 | Ruiz |
| 5,885,217 A | 3/1999 | Gisselberg et al. |
| 5,888,196 A | 3/1999 | Bonutti |
| 5,902,282 A | 5/1999 | Balbierz |
| 5,908,435 A | 6/1999 | Samuels |
| 5,916,145 A | 6/1999 | Chu et al. |
| 5,922,019 A | 7/1999 | Hankh et al. |
| 5,961,499 A | 10/1999 | Bonutti et al. |
| 5,964,730 A | 10/1999 | Williams et al. |
| 5,971,938 A | 10/1999 | Hart et al. |
| 5,997,508 A | 12/1999 | Lunn et al. |
| 6,030,364 A | 2/2000 | Durgin et al. |
| 6,056,718 A | 5/2000 | Funderburk et al. |
| 6,063,056 A | 5/2000 | Engelberg |
| 6,080,174 A | 6/2000 | Dubrul et al. |
| 6,090,072 A | 7/2000 | Kratoska et al. |
| 6,120,480 A | 9/2000 | Zhang et al. |
| 6,123,689 A | 9/2000 | To et al. |
| 6,168,579 B1 | 1/2001 | Tsugita |
| 6,183,443 B1 * | 2/2001 | Kratoska et al. ........ 604/164.03 |
| 6,187,000 B1 | 2/2001 | Davison et al. |
| 6,197,016 B1 | 3/2001 | Fourkas et al. |
| 6,228,052 B1 | 5/2001 | Pohndorf |
| 6,248,116 B1 | 6/2001 | Chevillon et al. |
| 6,280,452 B1 | 8/2001 | Mears |
| 6,293,909 B1 | 9/2001 | Chu et al. |
| 6,312,443 B1 | 11/2001 | Stone |
| 6,358,238 B1 | 3/2002 | Sherry |
| 6,443,979 B1 * | 9/2002 | Stalker et al. .............. 623/1.11 |
| 6,447,540 B1 | 9/2002 | Fontaine et al. |
| 6,471,684 B2 | 10/2002 | Dulak et al. |
| 6,494,860 B2 | 12/2002 | Rocamora et al. |
| 6,494,893 B2 | 12/2002 | Dubrul et al. |
| 6,517,551 B1 | 2/2003 | Driskill |
| 6,524,268 B2 | 2/2003 | Hayner et al. |

| | | |
|---|---|---|
| 6,524,320 B2 | 2/2003 | DiPoto |
| 6,530,902 B1 | 3/2003 | Jonkman |
| 6,537,247 B2 | 3/2003 | Shannon |
| 6,582,395 B1 | 6/2003 | Burkett et al. |
| 6,613,038 B2 | 9/2003 | Bonutti et al. |
| 6,613,062 B1 | 9/2003 | Leckrone et al. |
| 6,616,678 B2 | 9/2003 | Nishtala et al. |
| 6,638,268 B2 | 10/2003 | Niazi |
| 6,679,902 B1 | 1/2004 | Boyle et al. |
| 6,692,462 B2 | 2/2004 | Mackenzie et al. |
| 6,692,482 B2 | 2/2004 | Heller et al. |
| 6,706,017 B1 | 3/2004 | Dulguerov |
| 6,808,520 B1 | 10/2004 | Fourkas et al. |
| 6,827,683 B2 | 12/2004 | Otawara |
| 6,951,555 B1 | 10/2005 | Suresh et al. |
| 7,033,369 B2 | 4/2006 | Davison et al. |
| 7,056,319 B2 | 6/2006 | Aliperti et al. |
| 7,135,015 B2 | 11/2006 | Dulak et al. |
| 7,309,334 B2 | 12/2007 | Von Hoffmann |
| 7,316,677 B1 | 1/2008 | Dulak et al. |
| 7,329,268 B2 | 2/2008 | Van Nguyen et al. |
| 7,457,661 B2 | 11/2008 | Doty |
| 7,713,193 B2 | 5/2010 | Nance et al. |
| 7,780,692 B2 | 8/2010 | Nance et al. |
| 2001/0012950 A1 | 8/2001 | Nishtala et al. |
| 2001/0037126 A1 | 11/2001 | Stack et al. |
| 2002/0009535 A1 | 1/2002 | Michal et al. |
| 2002/0010440 A1 | 1/2002 | Segesser |
| 2002/0010476 A1 | 1/2002 | Mulholland et al. |
| 2002/0077653 A1 | 6/2002 | Hudson et al. |
| 2002/0099431 A1 | 7/2002 | Armstrong et al. |
| 2002/0161377 A1 | 10/2002 | Rabkin |
| 2003/0050600 A1 | 3/2003 | Ressemann et al. |
| 2003/0065353 A1 | 4/2003 | Horzewski et al. |
| 2003/0135156 A1 | 7/2003 | Bencini et al. |
| 2003/0195551 A1 | 10/2003 | Davison et al. |
| 2003/0212384 A1 | 11/2003 | Hayeden |
| 2003/0216770 A1 | 11/2003 | Persidsky et al. |
| 2004/0006344 A1 | 1/2004 | Nguyen et al. |
| 2004/0073286 A1 | 4/2004 | Armstrong et al. |
| 2004/0087968 A1 | 5/2004 | Core |
| 2004/0181273 A1 | 9/2004 | Brasington et al. |
| 2004/0220549 A1 | 11/2004 | Dittman et al. |
| 2004/0236346 A1 | 11/2004 | Parker |
| 2005/0043780 A1 | 2/2005 | Gifford et al. |
| 2005/0085842 A1 | 4/2005 | Eversull et al. |
| 2005/0124937 A1 | 6/2005 | Kick et al. |
| 2005/0125021 A1 | 6/2005 | Nance et al. |
| 2005/0149105 A1 | 7/2005 | Leeflang et al. |
| 2005/0222576 A1 | 10/2005 | Kick et al. |
| 2006/0036276 A1 | 2/2006 | Nguyen et al. |
| 2006/0052750 A1 | 3/2006 | Lenker et al. |
| 2006/0142795 A1 | 6/2006 | Nguyen et al. |
| 2006/0200188 A1 | 9/2006 | Nance et al. |
| 2006/0200189 A1 | 9/2006 | Nance et al. |
| 2006/0247602 A1 | 11/2006 | Dulak et al. |
| 2007/0112335 A1 | 5/2007 | Dulak et al. |

FOREIGN PATENT DOCUMENTS

| | | |
|---|---|---|
| EP | 0 249 456 | 12/1987 |
| EP | 0385920 | 9/1990 |
| EP | 02076553 | 1/1991 |
| EP | 0 546 766 A | 6/1993 |
| EP | 0 421 650 A | 4/1994 |
| WO | 92/19312 | 11/1992 |
| WO | 95/30374 | 11/1995 |
| WO | WO 99/16499 A | 4/1999 |
| WO | WO/99/17665 | 4/1999 |
| WO | WO 03/090834 A2 | 11/2003 |
| WO | WO2004/019760 A2 | 3/2004 |

OTHER PUBLICATIONS

Jan. 15, 2009 Response to Jul. 14, 2008 European Patent Office Communication in Euro. App. No. 05 794 899.4 filed on Sep. 8, 2005.
Sep. 13, 2006 Non-final Rejection in U.S. Appl. No. 10/728,728, filed Dec. 5, 2003.
Dec. 12, 2006 Response to Sep. 13, 2006 Non-final Rejection in U.S. Appl. No. 10/728,728, filed Dec. 5, 2003.
May 1, 2007 Notice of Allowance in U.S. Appl. No. 10/728,728, filed Dec. 5, 2003.
Oct. 18, 2007 Non-final Rejection in U.S. Appl. No. 10/728,728, filed Dec. 5, 2003.
Jan. 18, 2008 Response to Oct. 18, 2007 Non-final Rejection in U.S. Appl. No. 10/728,728, filed Dec. 5, 2003.
May 28, 2008 Non-final Rejection in U.S. Appl. No. 10/728,728, filed Dec. 5, 2003.
Nov. 25, 2008 Response to May 28, 2008 Non-final Rejection in U.S. Appl. No. 10/728,728, filed Dec. 5, 2003.
Feb. 19, 2009 Final Rejection in U.S. Appl. No. 10/728,728, filed Dec. 5, 2003.
Feb. 5, 2009 Restriction Requirement in U.S. Appl. No. 11/884,017, filed Jul. 2, 2004.
Mar. 2, 2009 Response to Feb. 5, 2009 Restriction Requirement in U.S. Appl. No. 11/884,017, filed Jul. 2, 2004.
Apr. 17, 2009 Non-final Rejection in U.S. Appl. No. 11/884,017, filed Jul. 2, 2004.
Jan. 10, 2007 Non-final Rejection in U.S. Appl. No. 11/415,659, filed May 2, 2006.
Jun. 11, 2007 Response to Jan. 10, 2007 Non-final Rejection in U.S. Appl. No. 11/415,659, filed May 2, 2006.
Aug. 20, 2007 Final Rejection in U.S. Appl. No. 11/415,659, filed May 2, 2006.
Nov. 7, 2007 Response to Aug. 20, 2007 Final Rejection in U.S. Appl. No. 11/415,659, filed May 2, 2006.
Nov. 16, 2007 Advisory Action in U.S. Appl. No. 11/415,659, filed May 2, 2006.
Feb. 20, 2008 Response to Aug. 20, 2007 Final Rejection in U.S. Appl. No. 11/415,659, filed May 2, 2006.
May 20, 2008 Non-final Rejection in U.S. Appl. No. 11/415,659, filed May 2, 2006.
Nov. 19, 2008 Response to May 20, 2008 Non-final Rejection in U.S. Appl. No. 11/415,659, filed May 2, 2006.
Apr. 6, 2009 Final Rejection in U.S. Appl. No. 11/415,659, filed May 2, 2006.
May 11, 2009 Response to Apr. 6, 2009 Final Rejection in U.S. Appl. No. 11/415,659, filed May 2, 2006.
Jan. 8, 2007 Non-final Rejection in U.S. Appl. No. 11/415,764, filed May 2, 2006.
Jun. 8, 2007 Response to Jan. 8, 2007 Non-final Rejection in U.S. Appl. No. 11/415,764, filed May 2, 2006.
Aug. 20, 2007 Non-final Rejection in U.S. Appl. No. 11/415,764, filed May 2, 2006.
Feb. 20, 2008 Response to Aug. 20, 2007 Non-final Rejection in U.S. Appl. No. 11/415,764, filed May 2, 2006.
Jun. 13, 2008 Non-final Rejection in U.S. Appl. No. 11/415,764, filed May 2, 2006.
Dec. 12, 2008 Response to Jun. 13, 2008 Non-final Rejection in U.S. Appl. No. 11/415,764, filed May 2, 2006.
Oct. 3, 2008 Non-final Rejection in U.S. Appl. No. 11/223,897, filed Sep. 9, 2005.
Feb. 3, 2009 Response to Oct. 3, 2008 Non-final Rejection in U.S. Appl. No. 11/223,897, filed Sep. 9, 2005.
Apr. 17, 2009 Final Rejection in U.S. Appl. No. 11/223,897, filed Sep. 9, 2005.
May 12, 2009 Response to Apr. 17, 2009 Final Rejection in U.S. Appl. No. 11/223,897, filed Sep. 9, 2005.
European Search Report Application No. 05794899.4.
International Search Report for Application No. PCT/US05/31958 (the PCT counterpart of the parent application) mailed Apr. 3, 2007.
Jun. 30, 2009 Non-final rejection in U.S. Appl. No. 11/223,897 filed on Sep. 9, 2005.

Sep. 15, 2009 Response to Jun. 30, 2009 Non-final rejection in U.S. Appl. No. 11/223,897 filed on Sep. 9, 2005.
Dec. 28, 2009 Final Office Action for U.S. Appl. No. 11/223,897 filed Sep. 9, 2005.
Mar. 4, 2010 Response to Final Office Action for U.S. Appl. No. 11/223,897 filed Sep. 9, 2005.
Mar. 18, 2010 Interview Summary for U.S. Appl. No. 11/223,897 filed Sep. 9, 2005.
Mar. 26, 2010 Advisory Action for U.S. Appl. No. 11/223,897 filed Sep. 9, 2005.
Jun. 30, 2010 Appeal Brief filed for U.S. Appl. No. 11/223,897 filed Sep. 9, 2005.
Mar. 8, 2010 European Office Action for application No. 05 794 916.6.
Aug. 13, 2009 European Office Action for application No. 05 794 916.6.
Mar. 25, 2008 European Search Report for application No. 05 794 916.6.
Dec. 15, 2009 Response to the Examination Report for application No. 05 794 916.6.
Aug. 3, 2010 European Office Action for application No. 05 794 899.4.
Dec. 15, 2009 Response to the Examination Report for application No. 05 794 899.4.
Aug. 13, 2009 European Office Action for application No. 05 794 899.4.
European Search Report Application No. 05794899.4, Sep. 8, 2005.
Sep. 16, 2010 Board of Patent Appeals and Interferences Examiner's Answer for U.S. Appl. No. 11/223,897 filed on Sep. 9, 2005.

* cited by examiner

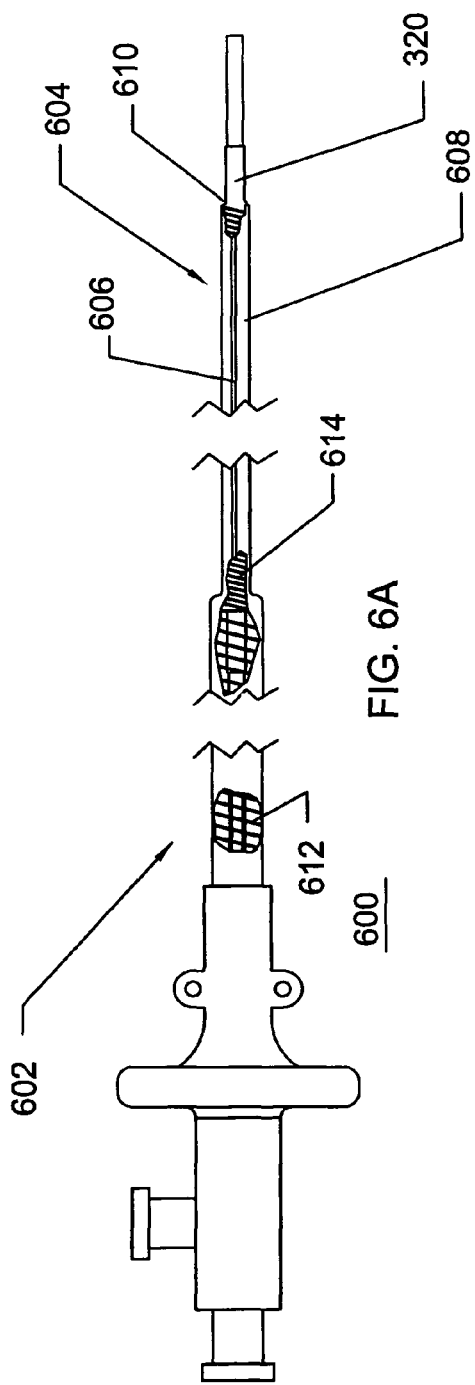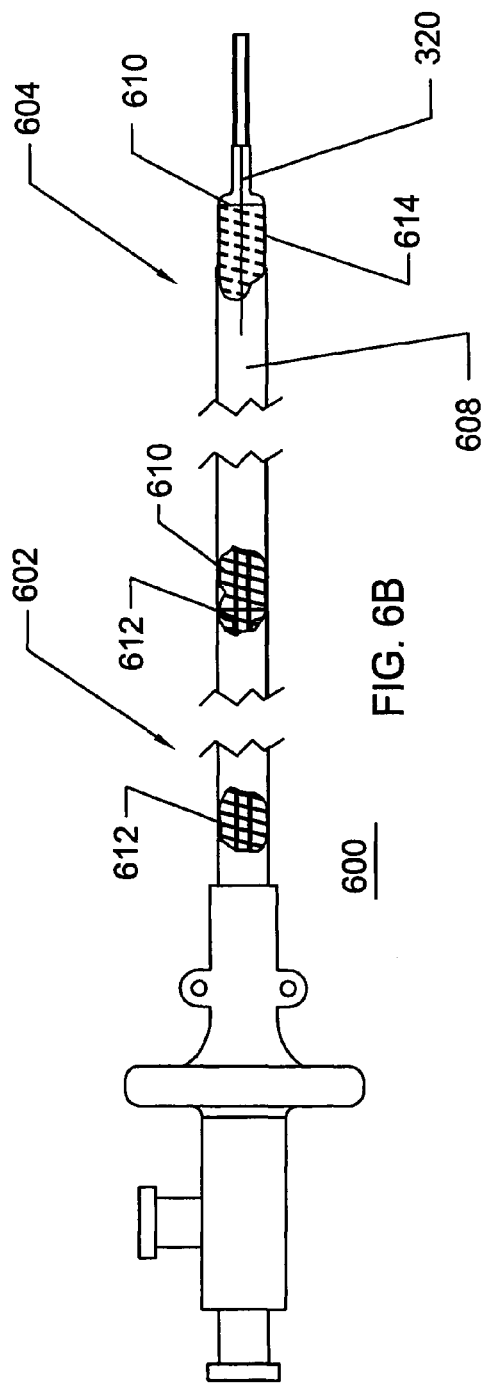

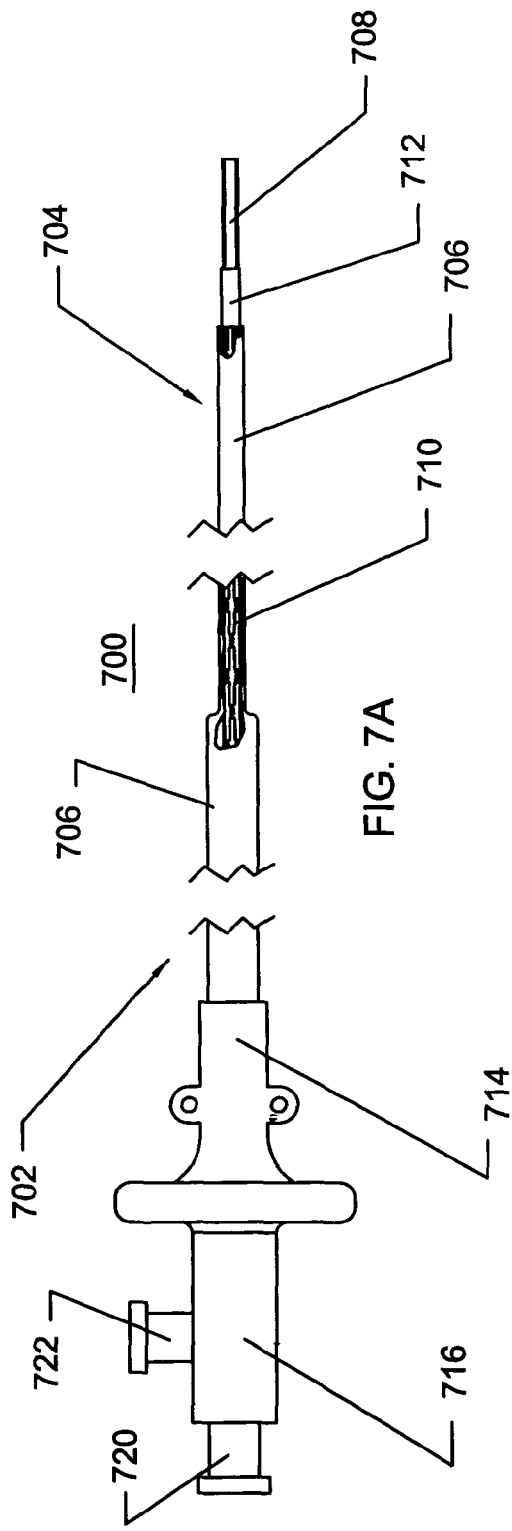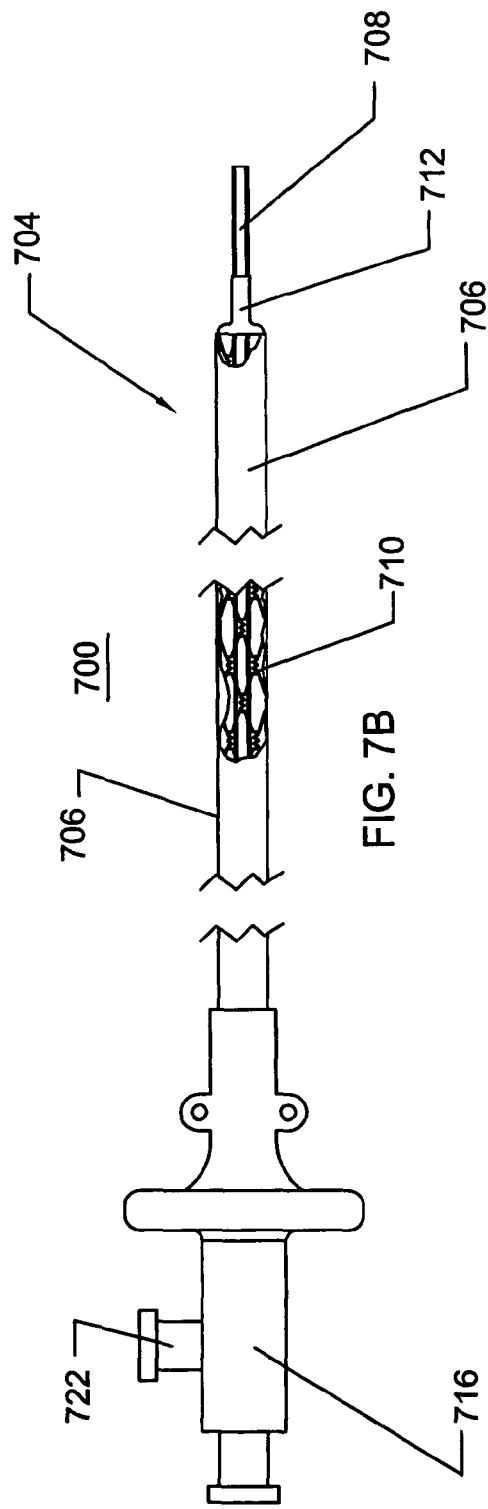

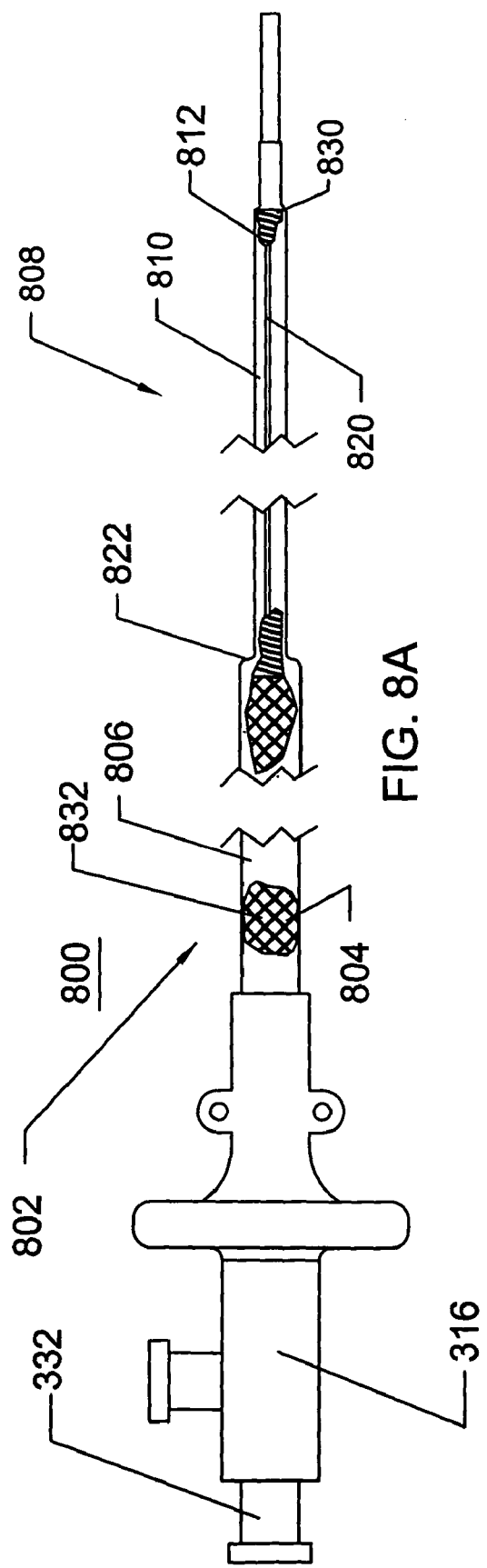
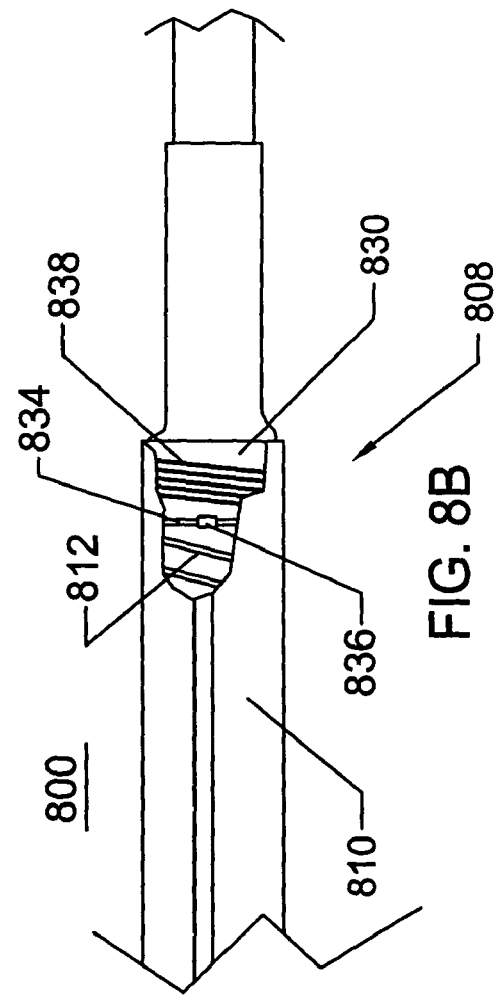
FIG. 8A
FIG. 8B

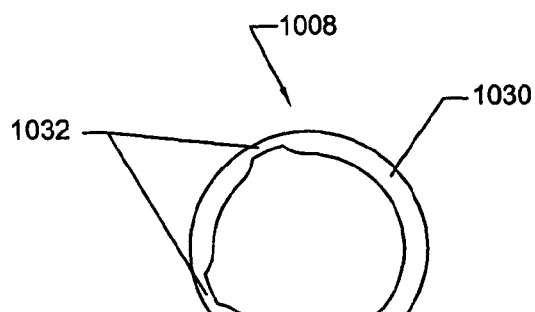
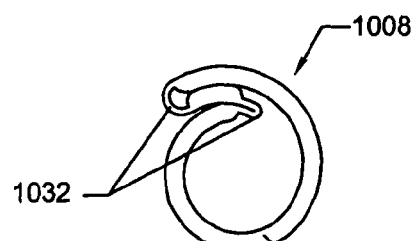
FIG. 10A
FIG. 10B
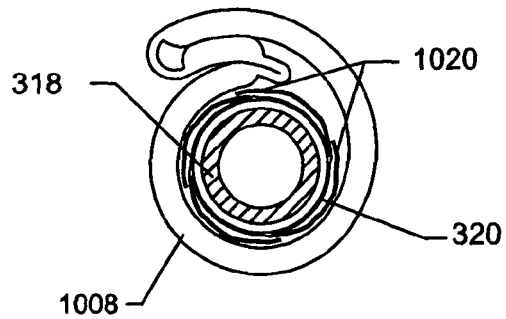
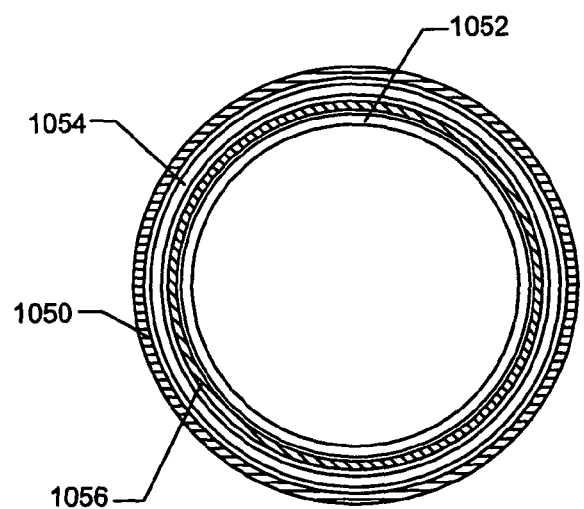
FIG. 10C
FIG. 10D
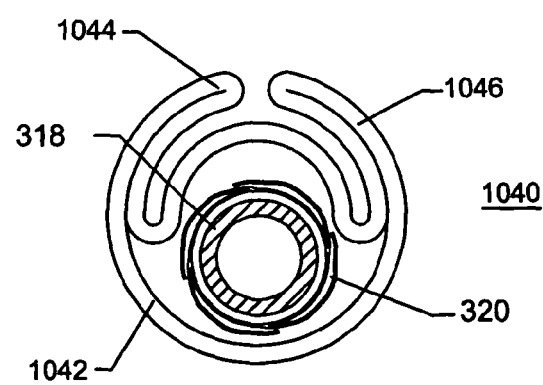
FIG. 10E

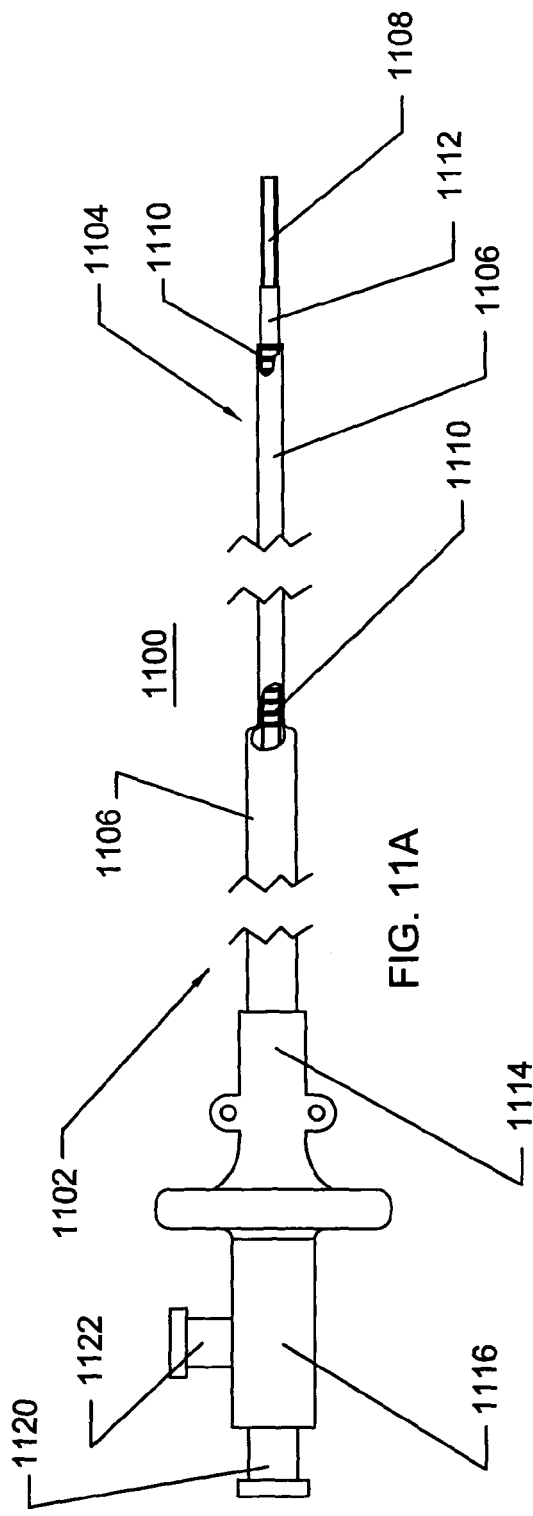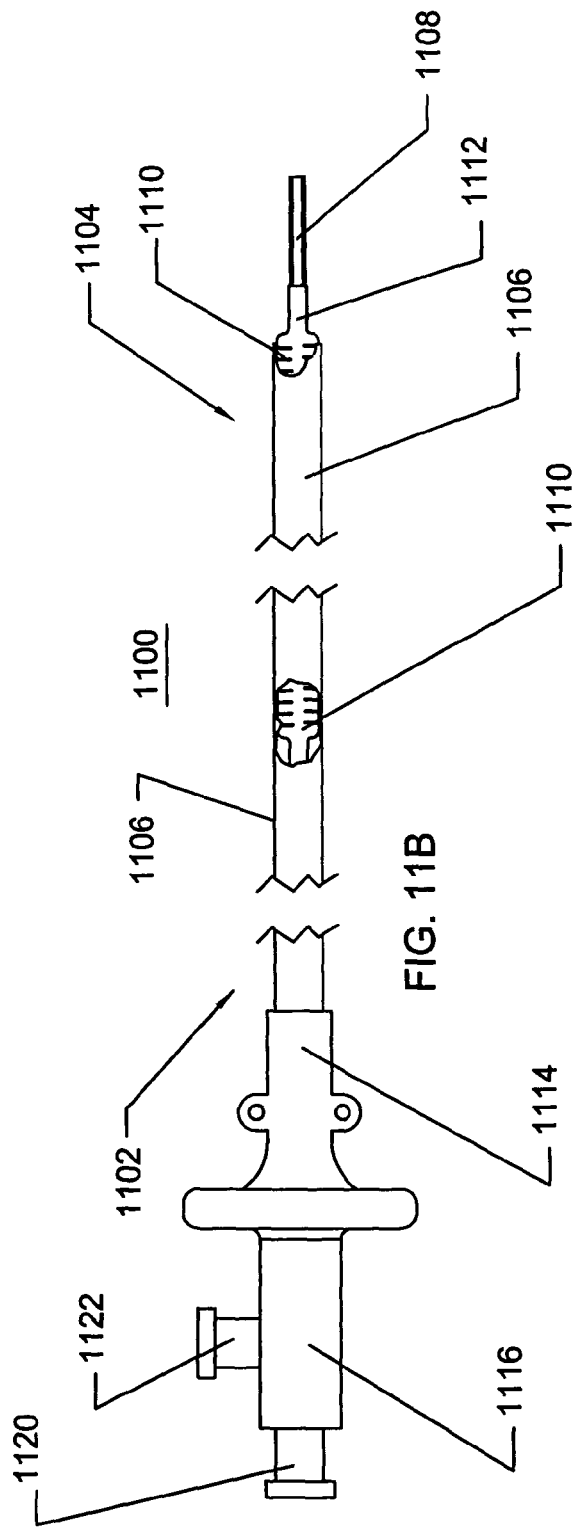

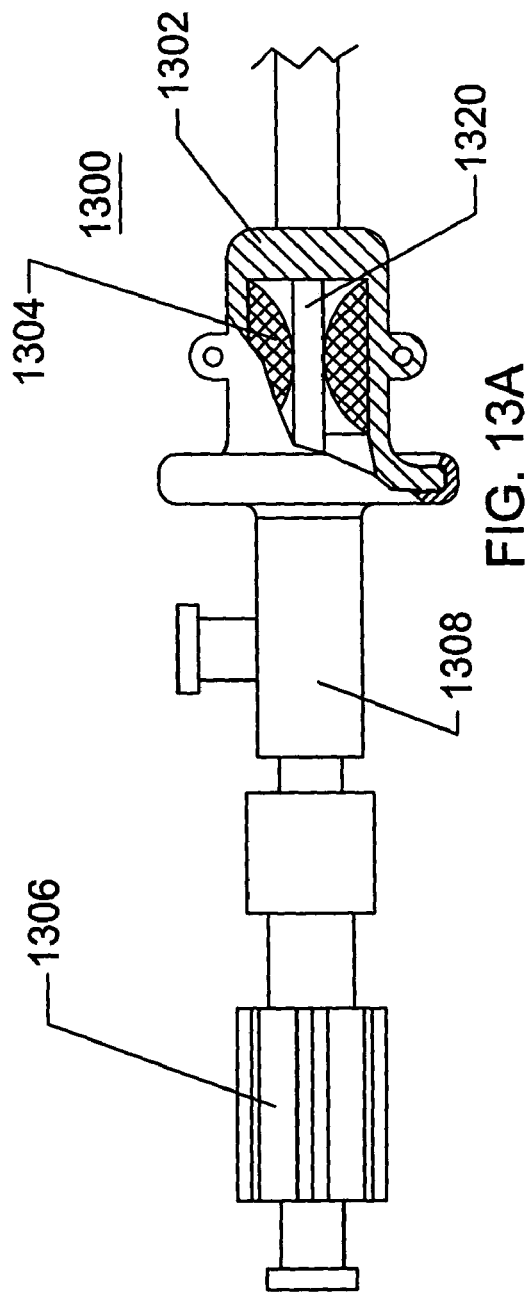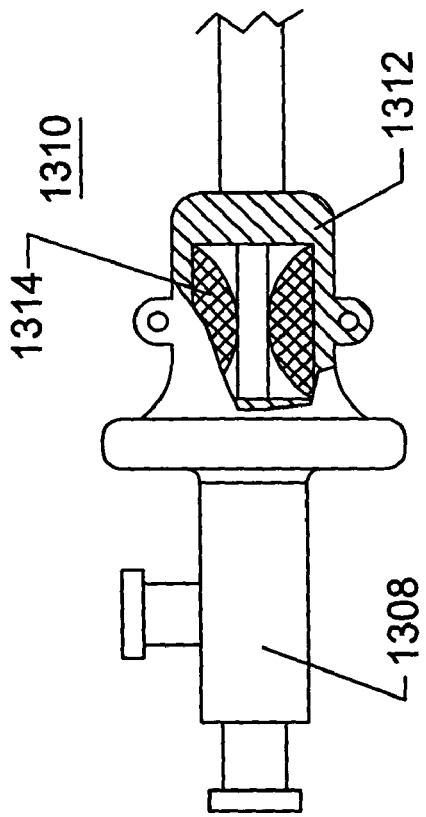
FIG. 13A
FIG. 13B

EXPANDABLE TRANSLUMINAL SHEATH

PRIORITY CLAIM

This application claims priority to under claims priority under 35 U.S.C. 119(e) of Provisional Application 60/660,512, filed Mar. 9, 2005 and Provisional Application 60/608,355, filed on Sep. 9, 2004, the entirety of which are hereby expressly incorporated herein by reference.

BACKGROUND OF THE INVENTION

1. Field of the Invention

The invention relates to medical devices for transluminally accessing body lumens and cavities and, more particularly, to methods and devices for accessing the mammalian urinary tract.

2. Description of the Related Art

A wide variety of diagnostic or therapeutic procedures involves the introduction of a device through a natural access pathway such as a body lumen or cavity. A general objective of access systems, which have been developed for this purpose, is to minimize the cross-sectional area of the access lumen, while maximizing the available space for the diagnostic or therapeutic instrumentation. These procedures are especially suited for the urinary tract of the human or other mammal. The urinary tract is relatively short and substantially free from the tortuosity found in many endovascular applications.

Ureteroscopy is an example of one type of therapeutic interventional procedure that relies on a natural access pathway, which is the urethra, the bladder, which is a body cavity, and the ureter, another body lumen. Ureteroscopy is a minimally invasive procedure that can be used to provide access to the upper urinary tract, specifically the ureter and kidney. Ureteroscopy is utilized for procedures such as stone extraction, stricture treatment, or stent placement. Other types of therapeutic interventional procedures suitable for use with expandable sheath technology include endovascular procedures such as introduction of cardiac valve replacements or repair devices via a percutaneous access to the vasculature. Gastrointestinal procedures, again percutaneously performed, include dilation of the common bile duct and removal of gallstones.

To perform a procedure in the ureter, a cystoscope is placed into the bladder through the urethra. A guidewire is next placed, through the working channel of the cystoscope and under direct visual guidance, into the target ureter. Once guidewire control is established, the cystoscope is removed and the guidewire is left in place. A ureteral sheath or catheter is next advanced through the urethra over the guidewire, through the bladder and on into the ureter. The guidewire may now be removed to permit instrumentation of the ureteral sheath or catheter. A different version of the procedure involves leaving the guidewire in place and passing instrumentation alongside or over the guidewire. In yet another version of the procedure, a second guidewire or "safety wire" may be inserted into the body lumen or cavity and left in place during some or all of the procedure.

Certain current techniques involve advancing a flexible, 10 to 18 French, ureteral sheath or catheter with integral flexible, tapered obturator over the guidewire. Because axial pressure is required to advance and place each catheter, care must be taken to avoid kinking the sheath, catheter, or guidewire during advancement so as not to compromise the working lumen of the catheter through which instrumentation, such as ureteroscopes and stone extractors, can now be placed. The operator must also exercise care to avoid advancing the sheath or catheter against strictures or body lumen or cavity walls with such force that injury occurs to said body lumen or cavity walls.

One of the issues that arise during ureteroscopy is the presence of an obstruction or stenosis in the ureter, which is sometimes called a stricture, that prohibits a sheath or catheter with a sufficiently large working channel from being able to be advanced into the ureter. Such conditions may preclude the minimally invasive approach and require more invasive surgical procedures in order to complete the task. Urologists may be required to use sheaths or catheters with suboptimal central lumen size because they are the largest catheters that can be advanced to the proximal end of the ureter. Alternatively, urologists may start with a larger catheter and then need to downsize to a smaller catheter, a technique that results in a waste of time and expenditure. Finally, a urologist may need to dilate the ureter with a dilation system before placing the current devices, again a waste of time and a need for multiple devices to perform the procedure. In most cases, it is necessary for the urologist to perform fluoroscopic evaluation of the ureter to determine the presence or absence of strictures and what size catheter would work for a given patient.

Additional information regarding ureteroscopy can be found in Su, L, and Sosa, R. E., *Ureteroscopy and Retrograde Ureteral Access, Campbell's Urology*, 8th ed, vol. 4, pp. 3306-3319 (2002), Chapter 97. Philadelphia, Saunders, and Moran, M. E., editor, *Advances in Ureteroscopy, Urologic Clinics of North America*, vol. 31, No. 1 (February 2004).

SUMMARY OF THE INVENTION

A need therefore remains for improved access technology, which allows a device to be transluminally passed through a relatively small diameter duct, while accommodating the introduction of relatively large diameter instruments. It would be beneficial if a urologist did not need to inventory and use a range of catheter diameters. It would be far more useful if one catheter diameter could fit the majority of patients. Ideally, the catheter would be able to enter a vessel or body lumen with a diameter of 6 to 10 French or smaller, and be able to pass instruments through a central lumen that was 12 to 18 French. These requirements appear to be contradictory but can be resolved by an embodiment of the invention described herein. Advantageously the sheath would also be maximally visible under fluoroscopy and would be relatively inexpensive to manufacture. The sheath or catheter would preferably be kink resistant and minimize abrasion and damage to instrumentation being passed therethrough. Preferably, the sheath or catheter would further minimize the potential for injury to body lumen or cavity walls or surrounding structures. Such damage could potentially lead to strictures, leakage of body lumen or cavity contents into surrounding spaces, contamination, hemorrhage, or the like.

Accordingly, one embodiment of the present invention comprise using a radially expanding access sheath to provide access to the ureter, kidney, or bladder. In one such embodiment, the sheath would have an introduction outside diameter that ranged from 4 to 12 French with a preferred range of 5 to 10 French. The diameter of the sheath would be expandable to permit instruments ranging up to 60 French to pass therethrough, with a preferred range of between 3 and 20 French. The ability to pass the large instruments through a catheter introduced with a small outside diameter is derived from the ability to expand the distal end of the catheter to create a larger through lumen. The expandable distal end of the catheter can comprise 75% or more of the overall working length of the catheter. The proximal end of the catheter is generally larger to provide for pushability, control, and the ability to pass large diameter instruments therethrough.

Another embodiment of the present invention comprises a transluminal access system for providing minimally invasive access to anatomically proximal structures. The system includes an access sheath comprising an axially elongate tubular body that defines a lumen extending from the proximal end to the distal end of the sheath. At least a portion of the distal end of the elongate tubular body is expandable from a first, smaller cross-sectional profile to a second, greater cross-sectional profile. In such an embodiment, the first, smaller cross-sectional profile is created by making axially oriented folds in the sheath material. These folds may be located in only one circumferential position on the sheath, or there may be a plurality of such folds or longitudinally oriented crimps in the sheath. The folds or crimps may be made permanent or semi-permanent by heat-setting the structure, once folded. In one embodiment, a releasable jacket is carried by the access sheath to restrain at least a portion of the elongate tubular structure in the first, smaller cross-sectional profile. In another embodiment, the jacket is removed prior to inserting the sheath into the patient. In some embodiments, the elongate tubular body is sufficiently pliable to allow the passage of objects having a maximum cross-sectional diameter larger than an inner diameter of the elongate tubular body in the second, greater cross-sectional profile. The adaptability to objects of larger dimension is accomplished by re-shaping of the cross-section to the larger dimension in one direction accompanied by a reduction in dimension in a lateral direction. The adaptability may also be generated through the use of malleable or elastomerically deformable sheath material.

In another embodiment of the invention, a transluminal access sheath assembly for providing minimally invasive access comprises an elongate tubular member having a proximal end and a distal end and defines a working inner lumen. In this embodiment, the tubular member comprises a folded or creased sheath that is expanded by a dilatation balloon. The dilatation balloon, can be filled with fluids at appropriate pressure, to generate the force to expand the sheath. The dilatation balloon is preferably removable to permit subsequent instrument passage through the sheath. In some embodiments, longitudinal runners may be disposed within the sheath to serve as tracks for instrumentation, which further minimize friction while minimizing the risk of catching the instrument on the expandable plastic tubular member. Such longitudinal runners are preferably circumferentially affixed within the sheath so as not to shift out of alignment. In yet another embodiment, the longitudinal runners may be replaced by longitudinally oriented ridges and valleys, termed flutes. The flutes, or runners, can be oriented along the longitudinal axis of the sheath, or they can be oriented in a spiral, or rifled, fashion.

In each of the embodiments, the proximal end of the access assembly, apparatus, or device is preferably fabricated as a structure that is flexible, resistant to kinking, and further retains both column strength and torqueability. Such structures can include, but are not limited to, tubes fabricated with coils or braided reinforcements and preferably comprise inner walls that prevent the reinforcing structures from protruding, poking through, or becoming exposed to the inner lumen of the access apparatus. Such proximal end configurations may be single lumen, or multi-lumen designs, with a main lumen suitable for instrument or obturator passage and additional lumens being suitable for control and operational functions such as balloon inflation. Such proximal tube assemblies can be affixed to the proximal end of the distal expandable segments described heretofore. In an embodiment, the proximal end of the catheter includes an inner layer of thin polymeric material, an outer layer of polymeric material, and a central region comprising a coil, braid, stent, plurality of hoops, or other reinforcement. In such an embodiment, it is beneficial to create a bond between the outer and inner layers at a plurality of points, most preferably at the interstices or perforations in the reinforcement structure, which is generally fenestrated. Such bonding between the inner and outer layers causes a braided structure to lock in place. In another embodiment, the inner and outer layers are not fused or bonded together in at least some, or all, places. When similar materials are used for the inner and outer layers, the sheath structure can advantageously be fabricated by fusing of the inner and outer layer to create a uniform, non-layered structure surrounding the reinforcement. The polymeric materials used for the outer wall of the jacket are preferably elastomeric to maximize flexibility of the catheter. The polymeric materials used in the composite catheter inner wall may be the same materials as those used for the outer wall, or they may be different. In another embodiment, a composite tubular structure can be co-extruded by extruding a polymeric compound with a braid or coil structure embedded therein. The reinforcing structure is preferably fabricated from annealed metals, such as fully annealed stainless steel, titanium, or the like. In this embodiment, once expanded, the folds or crimps can be held open by the reinforcement structure embedded within the sheath, wherein the reinforcement structure is malleable but retains sufficient force to overcome any forces imparted by the sheath tubing.

In certain embodiments of the invention, it is beneficial that the sheath comprise a radiopaque marker or markers. The radiopaque markers may be affixed to the non-expandable portion or they may be affixed to the expandable portion. Markers affixed to the radially expandable portion preferably do not restrain the sheath or catheter from radial expansion or collapse. Markers affixed to the non-expandable portion, such as the catheter shaft of a balloon dilator may be simple rings that are not radially expandable. Radiopaque markers include shapes fabricated from malleable material such as gold, platinum, tantalum, platinum iridium, and the like. Radiopacity can also be increased by vapor deposition coating or plating metal parts of the catheter with metals or alloys of gold, platinum, tantalum, platinum-iridium, and the like. Expandable markers may be fabricated as undulated or wavy rings, bendable wire wound circumferentially around the sheath, or other structures such as are found commonly on stents, grafts or catheters used for endovascular access in the body. Expandable structures may also include dots or other incomplete surround shapes affixed to the surface of a sleeve or other expandable shape. Non-expandable structures include circular rings or other structures that completely surround the catheter circumferentially and are strong enough to resist expansion. In another embodiment, the polymeric materials of the catheter or sheath, including those of the sheath composite wall, may be loaded with radiopaque filler materials such as, but not limited to, bismuth salts, or barium salts, or the like, at percentages ranging from 1% to 50% by weight in order to increase radiopacity.

In order to enable radial or circumferential expansive translation of the reinforcement, it may be beneficial not to completely bond the inner and outer layers together, thus allowing for some motion of the reinforcement in translation as well as the normal circumferential expansion. Regions of non-bonding may be created by selective bonding between the two layers or by creating non-bonding regions using a slip layer fabricated from polymers, ceramics or metals. Radial expansion capabilities are important because the proximal end needs to transition to the distal expansive end and, to minimize manufacturing costs, the same catheter may be employed at both the proximal and distal end, with the expansive distal end undergoing secondary operations to permit radial or diametric expansion.

In another embodiment, the distal end of the catheter is fabricated using an inner tubular layer, which is thin and lubricious. This inner layer is fabricated from materials such as, but not limited to, FEP, PTFE, polyamide, polyethylene, polypropylene, Pebax, Hytrel, and the like. Radiopaque filler materials can be added to the polymer inner layer during extrusion to enhance visibility under fluoroscopy. The reinforcement layer comprises a coil, braid, stent, or plurality of expandable, foldable, or collapsible rings, which are generally malleable and maintain their shape once deformed. Preferred materials for fabricating the reinforcement layer include but are not limited to, stainless steel, tantalum, gold, platinum, platinum-iridium, titanium, nitinol, and the like. The materials are preferably fully annealed or, in the case of nitinol, fully martensitic. The outer layer is fabricated from materials such as, but not limited to, FEP, PTFE, polyamide, polyethylene, polypropylene, polyurethane, Pebax, Hytrel, and the like. The inner layer is fused or bonded to the outer layer through holes in the reinforcement layer to create a composite unitary structure. The structure is crimped radially inward to a reduced cross-sectional area. A balloon dilator is inserted into the structure before crimping or after an initial crimping and before a final sheath crimping. The balloon dilator is capable of forced expansion of the reinforcement layer, which provides sufficient strength necessary to overcome any forces imparted by the polymeric tubing.

Another embodiment of the invention comprises a method of providing transluminal access. The method comprises inserting a cystoscope into a patient, transurethrally, into the bladder. Under direct optical visualization, fluoroscopy, MRI, or the like, a guidewire is passed through the instrument channel of the cystoscope and into the bladder. The guidewire is manipulated, under the visual control described above, into the ureter through its exit into the bladder. The guidewire is next advanced to the appropriate location within the ureter. The cystoscope is next removed, leaving the guidewire in place. The ureteral access sheath is next advanced over the guidewire transurethrally so that its distal tip is now resident in the ureter or the kidney. The position of the guidewire is maintained carefully so that it does not come out of the ureter and fall into the bladder. The removable dilator comprises the guidewire lumen, and is used to guide placement of the access sheath into the urinary lumens. Expansion of the distal end of the access sheath from a first smaller diameter cross-section to a second larger diameter cross-section is next performed, using the balloon dilator. The balloon dilator is subsequently removed from the sheath to permit passage of instruments that would not normally have been able to be inserted into the ureter due to the presence of strictures, stones, or other stenoses. The method further optionally involves releasing the elongate tubular body from a constraining tubular jacket, removing the expandable member from the elongate tubular body; inserting appropriate instrumentation, and performing the therapeutic or diagnostic procedure. Finally, the procedure involves removing the elongate tubular body from the patient. Once the sheath is in place, the guidewire may be removed or, preferably, it may be left in place. Alternatively, a second guidewire, or safety wire, can be introduced into the ureter and be placed alongside or through the sheath.

In one embodiment, where the transluminal access sheath is used to provide access to the upper urinary tract, the access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder. Other applications of the transluminal access sheath include a variety of diagnostic or therapeutic clinical situations, which require access to the inside of the body, through either an artificially created, percutaneous access, or through another natural body lumen.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 6A illustrates a side cutaway view of another embodiment of a radially collapsed sheath comprising an expandable distal region with one or more longitudinal folds and a malleable coil reinforcing layer embedded within the distal region;

FIG. 6B illustrates the sheath of FIG. 6A, with cutaway sections, wherein the balloon has expanded the distal region of the sheath to its fully expanded configuration;

FIG. 7A illustrates another embodiment of a radially expandable transluminal sheath comprising a malleable expandable stent-like reinforcement, a balloon dilator, and an unfolding sleeve with the distal end of the sheath, comprising this structure, is crimped or compressed radially inward for delivery to the patient;

FIG. 7B illustrates the radially expandable transluminal sheath of FIG. 7A wherein the distal section has been expanded by the balloon dilator;

FIG. 8A illustrates another embodiment of a radially expandable transluminal sheath comprising a dilatation balloon, a malleable, reinforced, folded, expandable distal end, a braid reinforced proximal end;

FIG. 8B illustrates an enlarged view of the distal tip of the distal region of the sheath of FIG. 8A with a breakaway of the outer layer showing the reinforcing layer, the inner layer, and the expandable radiopaque marker;

FIG. 10A illustrates a lateral cross-section of an embodiment of a sheath tube configured with discreet thin areas, running longitudinally along the tube;

FIG. 10B illustrates a lateral cross-section of the sheath tube of FIG. 10A which has been folded at the thin areas to create a smaller diameter tube;

FIG. 10C illustrates a lateral cross-section of the sheath tube of FIG. 10B, which has been folded down over a balloon, which has further been folded into four flaps and has been compressed against its central tubing;

FIG. 10D illustrates a lateral cross-section of an embodiment of a sheath tube comprising an inner lubricious layer, a reinforcing layer, an intermediate elastomeric layer, and an outer lubricious layer;

FIG. 10E illustrates a lateral cross-section of an embodiment of an expandable sheath tube comprising a double longitudinal fold;

FIG. 11A illustrates a side view of an embodiment of a sheath sheath comprising split ring reinforcement, with its distal end collapsed radially;

FIG. 11B illustrates a radially expandable sheath with split ring reinforcement as in FIG. 11A, wherein the distal end has been expanded;

FIG. 13A illustrates the proximal end of an embodiment of radially expandable sheath for endovascular use further comprising a valve integral to the sheath hub and a valve connected to the dilator hub;

FIG. 13B illustrates the proximal end of an embodiment of a radially expandable sheath for laparoscopic use, further comprising a valve integral to the sheath hub, according to an embodiment of the invention.

DETAILED DESCRIPTION OF THE PREFERRED EMBODIMENT

With reference to the FIGS. 1-14, various embodiments of a catheter or a sheath will be described. A catheter or a sheath, can be described as being an axially elongate hollow substantially tubular structure having a proximal end and a distal end. The axially elongate structure further has a longitudinal axis and preferably has an internal through lumen that can extend from the proximal end to the distal end for the passage of instruments, implants, fluids, tissue, or other materials. The axially elongate hollow tubular structure is preferably generally flexible and capable of bending, to a greater or lesser degree, through one or more arcs in one or more directions perpendicular to the main longitudinal axis. In many embodiments, the tubular structure and the internal lumen have a substantially circular cross-section but in other embodiments the cross-section can have another shape (e.g., oval, rectangular etc.)

As is commonly used in the art of medical devices, the proximal end of the device is that end that is closest to the user, typically a surgeon or interventionalist. The distal end of the device is that end closest to the patient or that is first inserted into the patient. A direction being described as being proximal to a certain landmark will be closer to the surgeon, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter in mm and is often useful for catheters that have non-circular cross-sectional configurations. While the original measurement of "French" used pi (3.14159 . . . ) as the conversion factor between diameters in mm and French, the system has evolved today to where the conversion factor is exactly 3.0.

Figure 1:
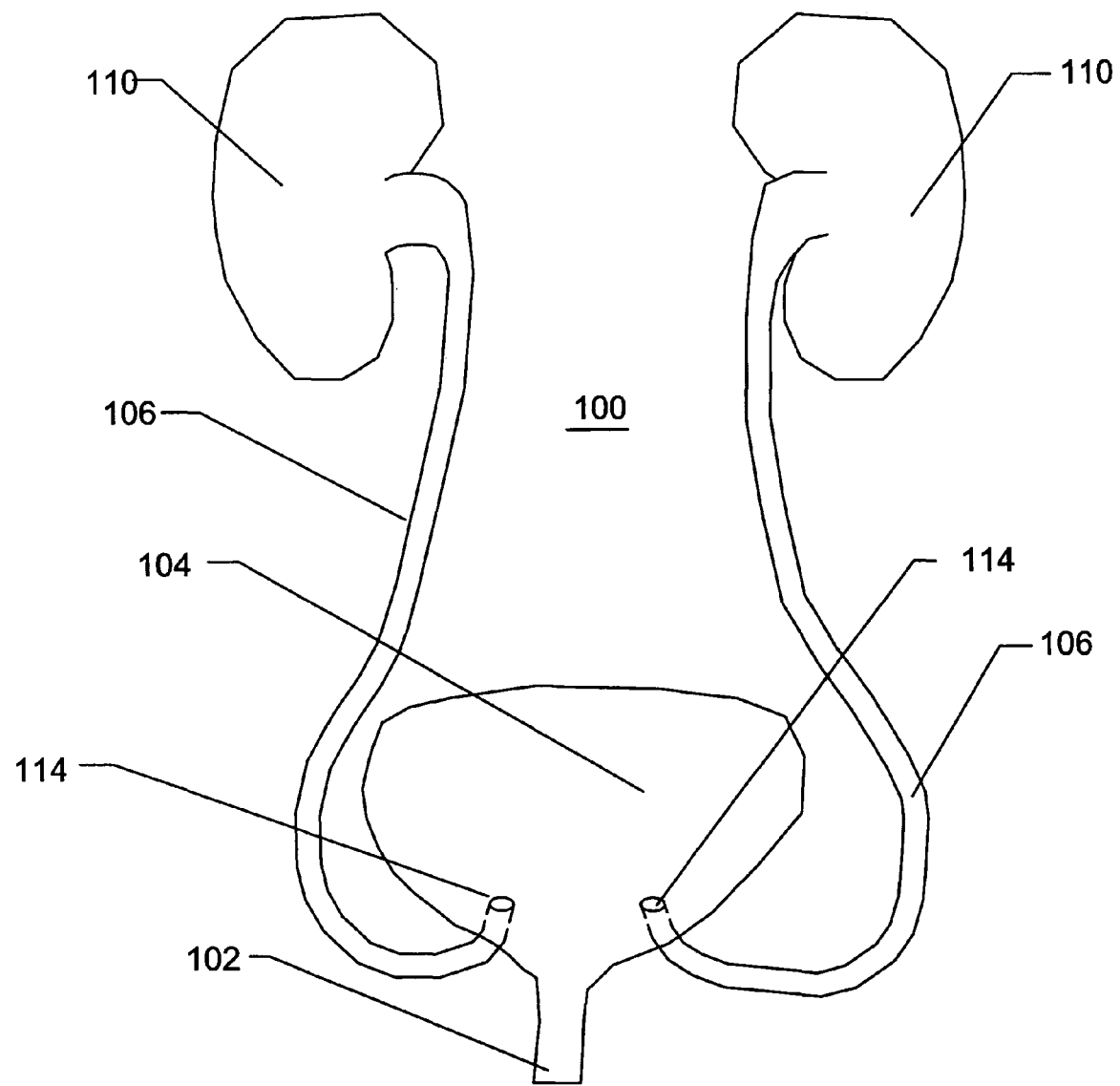
FIG. 1 is a front view schematic representation of the urethra, bladder, ureter, and kidneys.

FIG. 1 is a schematic frontal illustration of a urinary system 100 of the human comprising a urethra 102, a bladder 104, a plurality of ureters 106, a plurality of kidneys 110 and a plurality of entrances 114 to the ureter from the bladder. In this illustration, the left anatomical side of the body is toward the right of the illustration.

Referring to FIG. 1, the urethra 102 is lined on its interior by urothelium. Generally, the internal surfaces of the urethra 102, the bladder 104, and ureters 106 are considered mucosal tissue. The urethra 102 is relatively short in women and may be long in men since it runs through the entire length of the penis. The circumference of the unstretched urethra 102 is generally in the range of pi times 8 mm, or 24 mm, although the urethra 102 generally approximates the cross-sectional shape of a slit when no fluid or instrumentation is resident therein. The bladder 104 has the capability of holding between 100 and 300 cc of urine or more. The volume of the bladder 104 increases and decreases with the amount of urine that fills therein. During a urological procedure, saline is often infused into the urethra 102 and bladder 104 thus filling the bladder 104. The general shape of the bladder 104 is that of a funnel with a dome shaped top. Nervous sensors detect muscle stretching around the bladder 104 and a person generally empties their bladder 104, when it feels full, by voluntarily relaxing the sphincter muscles that surround the urethra 102. The ureters 106 operably connect the kidneys 110 to the bladder 104 and permit drainage of urine that is removed from the blood by the kidneys 110 into the bladder 104. The diameter of the ureters 106 in their unstretched configuration approximates a round tube with a 4 mm diameter, although their unstressed configuration may range from round to slit-shaped. The ureters 106 and the urethra 102 are capable of some expansion with the application of internal forces such as a dilator, etc. The entrances 114 to each of the ureters 106, of which there are normally two, are located on the wall of the bladder 104 in the lower region of the bladder 104.

Figure 2:
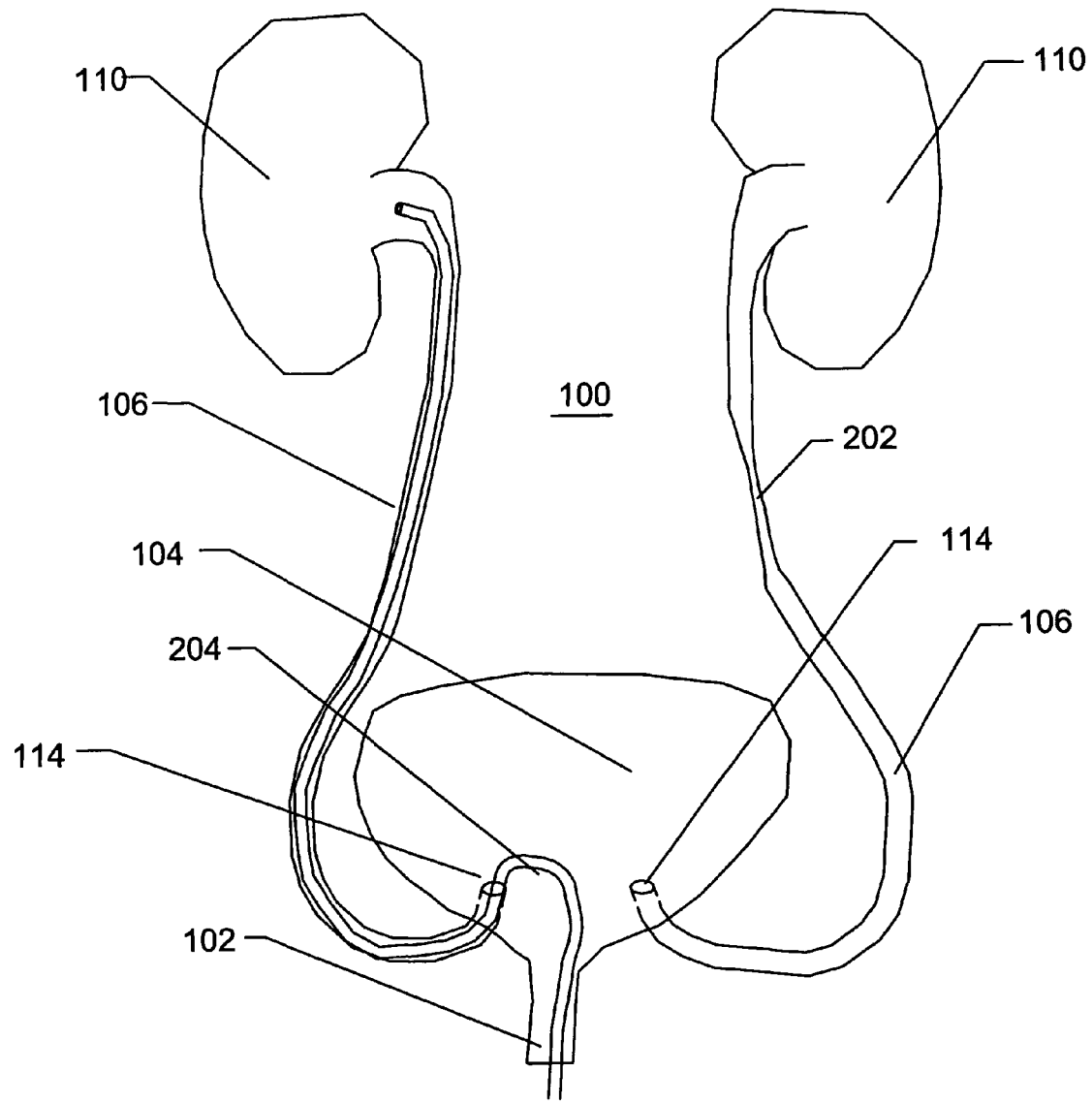
FIG. 2 is a front view schematic representation of the urethra, bladder, ureter, and kidneys with a catheter passed into the ureter by way of the urethra.
Figure 3:
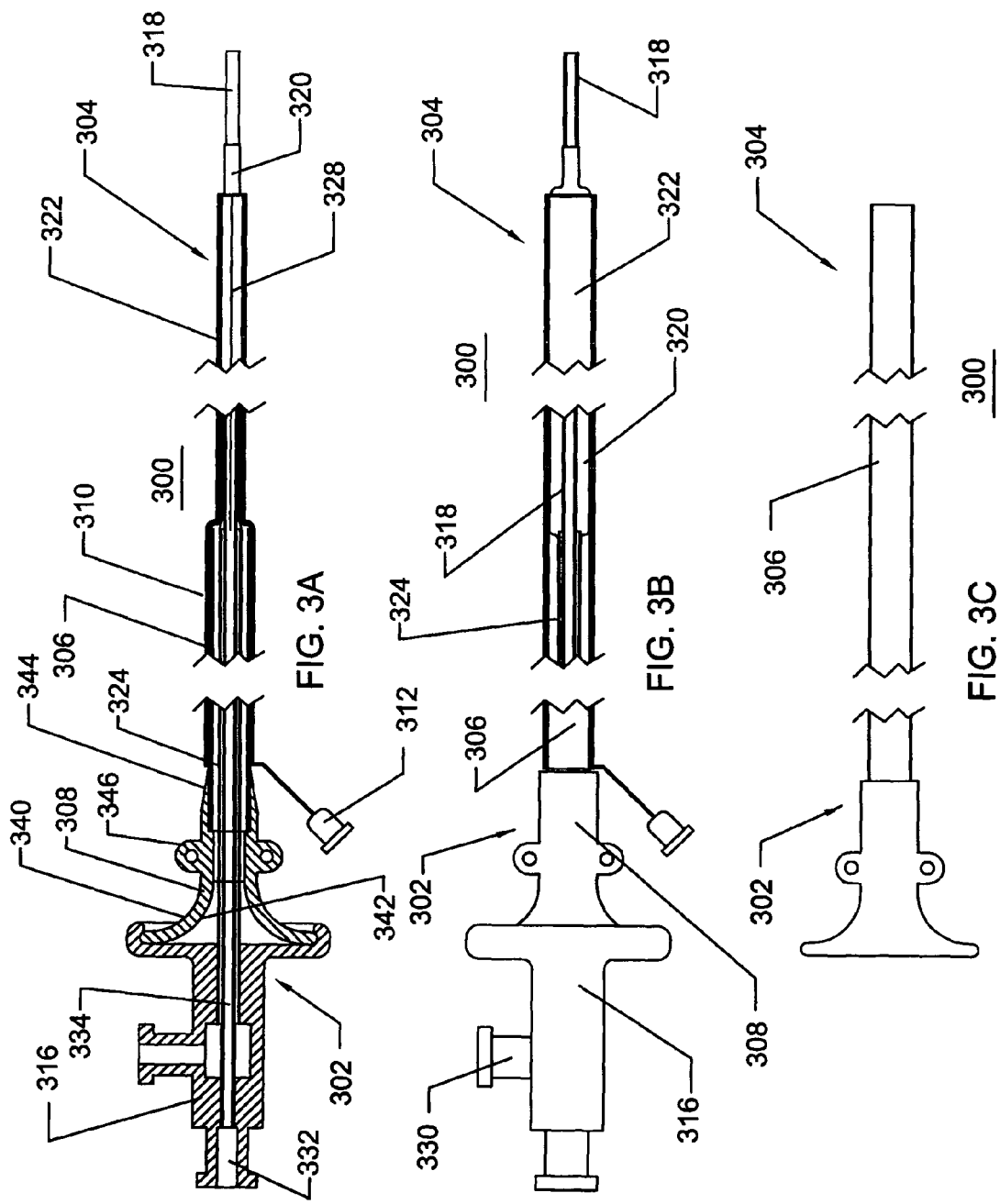
FIG. 3A is a cross-sectional illustration of an embodiment of a radially expandable transluminal catheter or sheath comprising a tube that is folded, at its distal end in longitudinal creases, a balloon dilator, and an outer retaining sleeve, the sheath tube and dilator being in their radially collapsed configuration.
FIG. 3B is a partial cross-sectional illustration of the radially expandable transluminal sheath of FIG. 3A, wherein the sheath and the dilator are in their radially expanded configuration.
FIG. 3C illustrates a side view of the radially expanded transluminal sheath of FIG. 3B, wherein the dilator has been removed, according to an embodiment of the invention.

FIG. 2 is a schematic frontal illustration, looking in the posterior direction from the anterior direction, of the urinary system 100 comprising the urethra 102, the bladder 104, a plurality of ureters 106 having entrances 114, a plurality of kidneys 110, a stricture 202 in the left ureter, and further comprising a catheter 204 extending from the urethra 102 into the right kidney 110. In this illustration, the left anatomical side of the body is toward the right of the illustration.

Referring to FIG. 2, the stricture 202 may be the result of a pathological condition such as an infection. The stricture may also be the result of iatrogenic injury such as that attributed to a surgical instrument or catheter that caused damage to the wall of the ureter 106. The stricture 202 may be surrounded by fibrous tissue and may prevent the passage of instrumentation that would normally have passed through a ureter 106. The catheter 204 is exemplary of the type used to access the ureter 106 and the kidney 110, having been passed transurethrally into the bladder 104 and on into the ureter 106. A catheter routed from the urethra 102 into one of the ureters 106 may turn a sharp radius within the open unsupported volume of the bladder 104. The radius of curvature necessary for a catheter to turn from the urethra 102 into the ureter 106 may be between 1 cm and 10 cm and in most cases between 1.5 cm and 5 cm. The catheter is generally first routed into the ureter 106 along a guidewire that is placed using a rigid cystoscope. The rigid cystoscope, once it is introduced, straightens out the urethra 102 and is aimed close to the entrance 114 to the ureter 106 to facilitate guidewire placement through the working lumen of the cystoscope.

FIG. 3A illustrates a longitudinal view of an embodiment of an expandable transluminal sheath 300 adapted for use in the urinary system 100 of FIGS. 1 and 2. The front (distal) section of the sheath 300 is depicted in exterior view and not in cross-section. The proximal region 302 and the central region are shown in longitudinal cross-section. The transluminal sheath 300 comprises a proximal end 302 and a distal end 304. In the illustrated embodiment, the proximal end 302 further comprises a proximal sheath tube 306, a sheath hub 308, an optional sleeve 310, an optional sleeve grip 312, an inner catheter shaft 318, an outer catheter shaft 324, and a catheter hub 316. The catheter hub 316 further comprises the guidewire access port 332. The catheter shaft 318 further comprises a guidewire lumen 334. The distal end 304 further comprises a distal sheath tube 322, the inner catheter shaft 318, and a balloon 320. The distal sheath tube 322 is folded longitudinally into one, or more, creases 328 to reduce the tubes 322 cross-sectional profile. The sheath hub 308 further comprises a distally facing surface 340, a proximally facing surface 342, a tapered distal edge 344, and a tie-down grommet 346.

Referring to FIG. 3A, the proximal end 302 generally comprises the proximal sheath tube 306 that can be permanently affixed or otherwise coupled to the sheath hub 308. The optional sleeve 310 is tightly wrapped around the proximal sheath tube 306 and is generally able to be split lengthwise and be removed or disabled as a restraint by pulling on the optional sleeve grip 312 that is affixed to the sleeve 310. The optional sleeve 310 is preferably fabricated from transparent material, or material with a color other than that of the sheath 300, and is shown so in FIG. 3A and 3B. The proximal end further comprises the inner catheter shaft 318, the outer catheter shaft 324, and the catheter hub 316. The catheter hub 316 is integrally molded with, welded to, bonded or otherwise coupled, to the guidewire port 332. The dilator, or catheter, hub 316 allows for gripping the dilator and it allows for expansion of the dilatation balloon 320 by pressurizing an annulus between the inner catheter shaft 318 and the outer catheter shaft 324, said annulus having openings into the interior of the balloon 320. The balloon 320 is preferably bonded, at its distal end, either adhesively or by fusion, using heat or ultrasonics, to the inner catheter shaft 318. The proximal end of the balloon 320 is preferably bonded or welded to the outer catheter shaft 324. In another embodiment, pressurization of the balloon 320 can be accomplished by injecting fluid, under pressure, into a separate lumen in the inner or outer catheter shafts 318 or 324, respectively, said lumen being operably connected to the interior of the balloon 320 by openings or scythes in the catheter tubing. Such construction can be created by extruding a multi-lumen tube, rather than by nesting multiple concentric tubes. The distal end 304 generally comprises the distal sheath tube 322 which is folded into creases 328 running along the longitudinal axis and which permit the area so folded to be smaller in diameter than the sheath tube 306. The inner catheter shaft 318 comprises a guidewire lumen 334 that may be accessed from the proximal end of the catheter hub 316 and preferably passes completely through to the distal tip of the catheter shaft 318. The guidewire lumen 334 is able to slidably receive guidewires up to and including 0.038-inch diameter devices.

As mentioned above, the proximal end of the sheath 300 comprises the sheath hub 308 and the dilator hub 316. In one embodiment, the dilator hub 316 is keyed so that when it is interfaced to, or attached to, the sheath hub 308, the two hubs 308 and 316 cannot rotate relative to each other. This is beneficial so that the balloon 320 or the dilator shaft 318 do not become twisted due to inadvertent rotation of the dilator hub 316 relative to the sheath hub 308. A twisted balloon 320 has the potential of not dilating fully because the twist holds the balloon 320 tightly to the dilator shaft 318 and prevents fluid from fully filling the interior of the balloon 320. Twisting of the dilator shaft 318 or balloon 320 has the potential for restricting guidewire movement within the guidewire lumen 334 or adversely affecting inflation/deflation characteristics of the balloon 320. Thus, the anti-rotation feature of the two hubs 308 and 316 can be advantageous in certain embodiments. The anti-rotation features could include mechanisms such as, but not limited to, one or more keyed tab on the dilator hub 316 and one or more corresponding keyed slot in the sheath hub 308.

In the illustrated embodiment, axial separation motion between the dilator hub 316 and the sheath hub 308 easily disengages the two hubs 308 and 316 while rotational relative motion is prevented by the sidewalls of the tabs and slots. A draft angle on the sidewalls of the tabs and the slots further promotes engagement and disengagement of the anti-rotation feature. In another embodiment, the sheath hub 308 is releaseably affixed to the dilator hub 316 so the two hubs 308 and 316 are coaxially aligned and prevented from becoming inadvertently disengaged or separated laterally. In this embodiment, the two hubs 308 and 316 are connected at a minimum of 3 points, which prevent lateral relative motion in both of two substantially orthogonal axes. In a preferred embodiment, the two hubs 308 and 316 are engaged substantially around their full 360-degree perimeter. Manual pressure is sufficient to snap or connect the two hubs 308 and 316 together as well as to separate the two hubs 308 and 316.

In another embodiment, the distal end of the sheath hub 308 is configured to taper into the sheath tubing 306 at the distal taper 344 so that the sheath hub 308 distal end 344 and the proximal end of the sheath tubing 306 can be advanced, at least partly, into the urethra or urethral meatus without causing tissue damage. The sheath hub 308 serves as the handle for the sheath 300 and is generally a cylinder of revolution with certain changes in outside diameter moving from distal to proximal end. In the illustrated embodiment, the distal facing surface 340 of the sheath hub 308 can define a cone tapering inward moving increasingly distally. The cone, in longitudinal cross-section, can be characterized by two exterior walls, symmetrically disposed about a centerline, each of said exterior walls being curvilinear and describing a concave outline. In a preferred embodiment, the exterior outline of the distal surface 340 of the sheath hub 308 can describe a linear outline, with surfaces running generally parallel to the longitudinal axis of the sheath tubing 306 and other surfaces running generally perpendicular to the longitudinal axis of the sheath tubing 306. In this preferred embodiment, there are no curvilinear axial cross-sectional outlines except at regions of fillets or other rounding to substantially eliminate any sharp edges that could cut through gloves or fingers. The proximally facing surface 342 of the sheath hub 308 can be curvilinear and flared with a longitudinal cross-section outline appearing like the internal surface of a bell, such shape acting as a funnel for instrumentation. In this embodiment, the axial cross-sectional view of the distally facing surface 342 describes two interior walls, symmetrically disposed about a centerline, each of the walls being convex when viewed from the proximal end of the sheath 300. In a preferred embodiment, the proximally facing surface 342 of the sheath hub 308 can appear substantially linear with edges that are oriented substantially perpendicular to the longitudinal axis of the sheath tubing 306. The access through the proximal surface 342 of the sheath hub 308 to the inner lumen of the sheath 300, can be curvilinear and flared, or it can be linear and describe a lumen that is generally parallel to the longitudinal axis. In another embodiment, the access port through the proximal end 342 of the sheath hub 308 can comprise a straight taper, such as a 6 percent Luer taper to allow for sealing with other devices inserted therein or to allow for ease of device insertion. The amount of end taper can vary between 1½ degrees and 20 degrees between each side and the longitudinal axis of the sheath 300. The maximum outer diameter of the sheath hub 308 can be between 0.25 and 2.0 inches, with a preferred range of between 0.5 and 1.0 inches. The sheath hub 308 can be sized so that at least half a finger diameter is cradled by each side of the flange of the hub 308. The distally facing surface 340 of the sheath hub 308 can furthermore be shaped to have substantially the same curve radius as a finger, so as to be received, or grasped, between two fingers of the hand, cigarette style, like the technique used for control of cystoscopes. In another embodiment, the sheath hub 308 can be sized and configured to be grasped between a thumb and finger, like a pencil or catheter, where there are no features or curves on the distally facing surface 340 of the sheath hub 308 to approximately match or conform to the shape or diameter of two fingers.

In the illustrated embodiment of FIG. 3A, the distal end 304 of the device comprises the catheter shaft 318 and the dilatation balloon 320. The catheter hub 316 may removably lock onto the sheath hub 308 to provide increased integrity to the system and maintain longitudinal relative position between the catheter shaft 318 and the sheath tubing 322 and 306. The catheter hub 316 can have a taper leading from the proximal outside end into any internal or through lumens. The catheter shaft 318 and the balloon 320 are slidably received within the proximal sheath tube 306. The catheter shaft 318 and balloon 320 are slidably received within the distal sheath tube 322 when the distal sheath tube 322 is radially expanded but are frictionally locked within the distal sheath tube 322 when the tube 322 is radially collapsed. The outside diameter of the distal sheath tube 322 ranges from about 4 French to about 16 French in the radially collapsed configuration with a preferred size range of about 5 French to about 10 French. The outside diameter is an important parameter for introduction of the device. Once expanded, the distal sheath tube 322 has an inside diameter ranging from about 8 French to about 20 French. In many applications, the inside diameter is more important than the outside diameter once the device has been expanded. The wall thickness of the sheath tubes 306 and 322 can range from about 0.002 to about 0.030 inches with a preferred thickness range of about 0.005 to about 0.020 inches.

FIG. 3B illustrates a cross-sectional view of the sheath 300 of FIG. 3A wherein the balloon 320 has been inflated causing the sheath tube 322 at the distal end 304 to expand and unfold the longitudinal creases or folds 328. Preferably, the distal sheath tube 322 has the properties of being able to bend or yield, especially at crease lines, and maintain its configuration once the forces causing the bending or yielding are removed. The proximal sheath tube 306 is can be affixed to the sheath hub 308 by insert molding, bonding with adhesives, welding, or the like. As mentioned above, the balloon 320 can be been inflated by pressurizing the annulus between the inner tubing 318 and the outer tubing 324 by application of an inflation device at the inflation port 330 which is integral to, bonded to, or welded to the catheter hub 316. The pressurization annulus empties into the balloon 320 at the distal end of the outer tubing 324. Exemplary materials for use in fabrication of the distal sheath tube 322 include, but are not limited to, polytetrafluoroethylene (PTFE), fluorinated ethylene polymer (FEP), polyethylene, polypropylene, polyethylene terephthalate (PET), and the like. A wall thickness of 0.008 to 0.012 inches is generally suitable for a device with a 16 French OD while a wall thickness of 0.019 inches is appropriate for a device in the range of 36 French OD. In one embodiment, the resulting through lumen of the sheath 300 is generally constant in French size going from the proximal end 302 to the distal end 304. The balloon 320 can be fabricated by techniques such as stretch blow molding from materials such as polyester, polyamide, irradiated polyethylene, and the like.

FIG. 3C illustrates a side cross-sectional view of the sheath 300 of FIG. 3B wherein the catheter shaft 318, the balloon 320, and the catheter hub 316 have been withdrawn and removed leaving the proximal end 302 and the distal end 304 with a large central lumen capable of holding instrumentation. The sleeve 310 and the sleeve grip 312 have also been removed from the sheath 300. The shape of the distal sheath tube 322 may not be entirely circular in cross-section, following expansion, but it is capable of carrying instrumentation the same size as the round proximal tube 306. Because it is somewhat flexible and further is able to deform, the sheath 300 can hold noncircular objects where one dimension is even larger than the round inner diameter of the sheath 300. The balloon 320 is preferably deflated prior to removing the catheter shaft 318, balloon 320 and the catheter hub 316 from the sheath 300.

Figure 4:
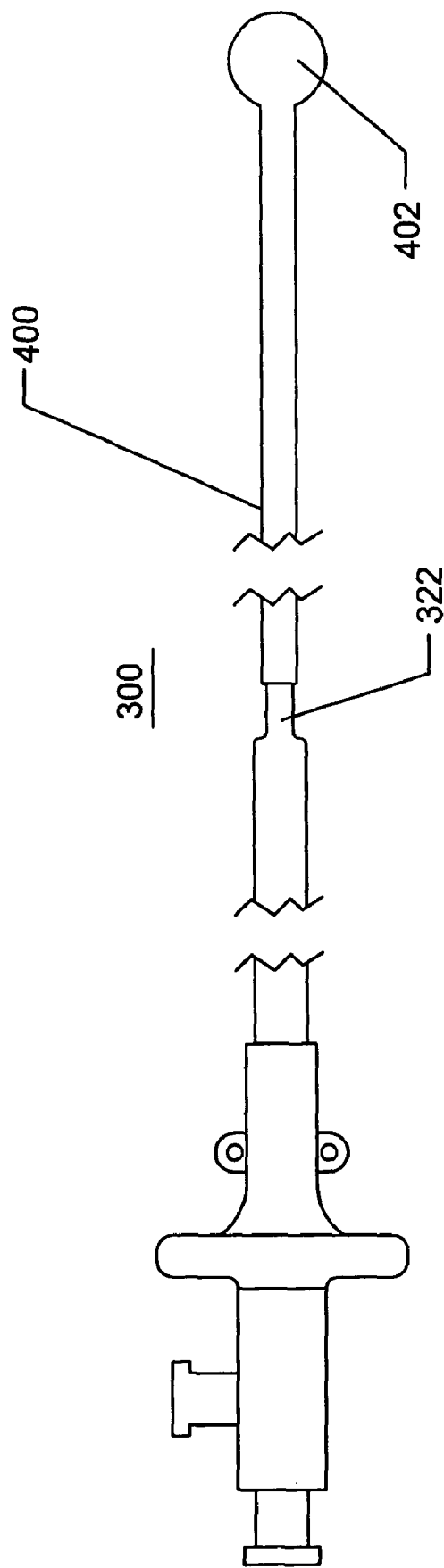
FIG. 4 illustrates a side view of another embodiment of a radially expandable transluminal catheter or sheath comprising a removable shroud covering the distal expandable region, according to an embodiment of the present invention.

FIG. 4 illustrates a side view of another embodiment of a radially expandable sheath 300 comprising a shroud 400. The shroud 400 is removed from the sheath 300 prior to insertion of the sheath 300 into the body lumen or cavity. In this embodiment, the shroud 400 is slidably affixed over the distal end of the distal sheath tube 322 after folding has been completed. The shroud 400, in this embodiment, is closed at its most distal end and must be removed prior to the procedure in order to advance the sheath 300 distally over a guidewire. The shroud 400 can be fabricated from polymeric tubing such as, but not limited to polyethylene, polypropylene, FEP, PTFE, polyurethane, polyamide, and the like. The inner diameter of the shroud 400 is the same as, or only slightly larger, for example 0.001 to 0.020 inches larger, than the outer diameter of the folded distal sheath tube 322. The wall thickness of the shroud 400 can be between 0.0005 and 0.10 inches and preferably range between 0.004 and 0.020 inches. The shroud 400 further comprises a plug or closure 402 at the distal end to prevent guidewire passage therethrough. The plug or closure 402 may have a profile larger than the shroud 400, or it may comprise serrations or bumps, to provide enhanced grip for removal and to remind the user that it should be removed prior to inserting it into the body lumen or cavity. The shroud 400 serves to protect the distal sheath tube 322 during shipping and handling and can help maintain the distal sheath tube 322 in its tightly folded and minimum diameter configuration during sterilization and for extended periods of storage and shipping. The shroud 400 ideally encloses the entire fully collapsed distal sheath tube 322, although less than full enclosure may also be functional. The shroud 400 may further comprise colors that differentiate it from the rest of the sheath 300, including transparent, translucent, fluorescent, or bright colors of orange, green, red, and the like. The shroud 400 may further comprise a label or tag with warnings that it must be removed prior to use of the sheath 300 on a patient. The label or tag can be integral to the shroud 400 or the plug or closure 402.

Figure 5A:
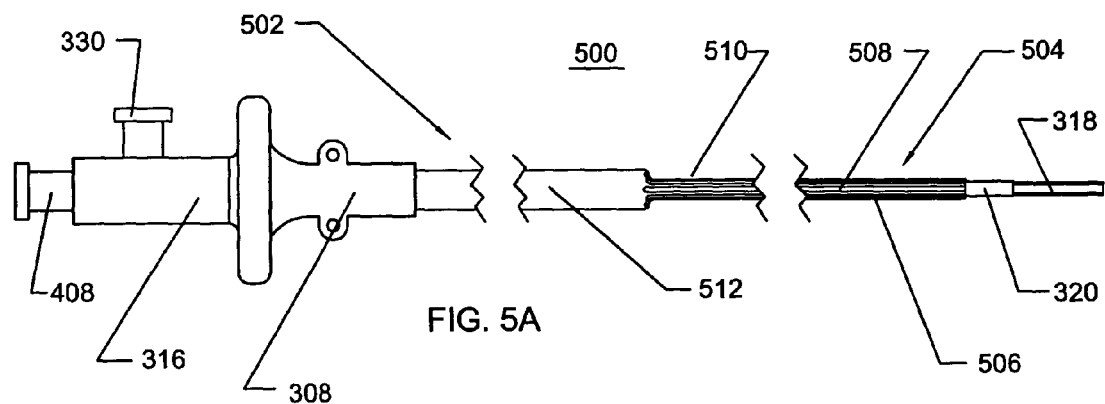
FIG. 5A is an illustration of another embodiment of a radially expandable transluminal sheath further comprising a plurality of longitudinally disposed runners.

FIG. 5A illustrates a side view of another embodiment of a sheath-dilator system 500 comprising a proximal section 502 and a distal section 504. The distal section 504 comprises a length of dilator tubing 318, a dilator balloon 320, and a longitudinally folded sheath tube 510. The distal section 504 further may comprise longitudinal runners 506 or flutes 520 separated by longitudinal slots or depressions 508. The proximal section 502 comprises a proximal sheath cover 512, a sheath hub 308, and a dilator hub 316, further comprising a guidewire port 408 and a balloon inflation connector 330. The sheath and catheter hubs 308, 316 can be arranged as described above.

Referring to FIG. 5A, the folded layer 510 is similar to the wall 306 of the sheath 300 of FIG. 3A. The folded layer 510 can be affixed, at its proximal end, to the distal end of the proximal sheath cover 512, which is non-expansible and surrounds the sheath 500 at its proximal end. The folded sheath tube 510 can also be integral to the proximal sheath cover 512, although the two regions may have different characteristics. The internal lumen of the folded sheath tube 510 is operably connected to the inner working lumen of the proximal sheath cover 512. The folded sheath tube 510 is constructed from materials that are plastically deformable, or malleable, such that the circumference is irreversibly increased by expansion of the dilator balloon 320 and the outward forces created thereby. The wall thickness of the folded sheath tube 510 is preferably generally constant as the folded sheath tube 510 is dilated. The folded sheath tube 510, once dilated, will generally provide sufficient hoop strength against collapse that it keeps surrounding tissues open. The optional longitudinal runners 506 or flutes 520, separated by the slits or depressions 508, provide a reduced friction track for the passage of instrumentation within the folded sheath tube 510. The runners 506 or flutes 520 can be fabricated from materials such as, but not limited to, PTFE, FEP, PET, stainless steel, cobalt nickel alloys, nitinol, titanium, polyamide, polyethylene, polypropylene, and the like. The runners 506 or flutes 520 may further provide column strength against collapse or buckling of the folded sheath tube 510 when materials such as calcific stones or other debris is withdrawn proximally through the sheath 500. The runners 506 or flutes 520 may be free and unattached, they may be integral to the ID material, or they may be affixed to the interior of the folded sheath tube 510 using adhesives, welding, or the like. In the case of flutes 520, the structure can be integrally formed with the folded sheath tube 510, such forming generally occurring at the time of extrusion or performed later as a secondary operation. Such secondary operation may include compressing the folded sheath tube 510 over a fluted mandrel under heat and pressure. The flutes 520 may advantageously extend not only in the distal region 504 but also in the interior of the proximal part of the sheath tubing, and/or, but not necessarily the hub 308.

The guidewire port 408 is generally configured as a Luer lock connector or other threaded or bayonet mount and the guidewire is inserted therethrough into the guidewire lumen of the dilator tubing 318 to which the guidewire port 408 is operably connected. The guidewire port 408 is preferably integrally fabricated with the dilator hub 316 but may be a separately fabricated item that is affixed to the dilator hub 316. A Tuohy-Borst or other valved fitting is easily attached to such connectors to provide for protection against loss of fluids, even when the guidewire is inserted.

Figure 5B:
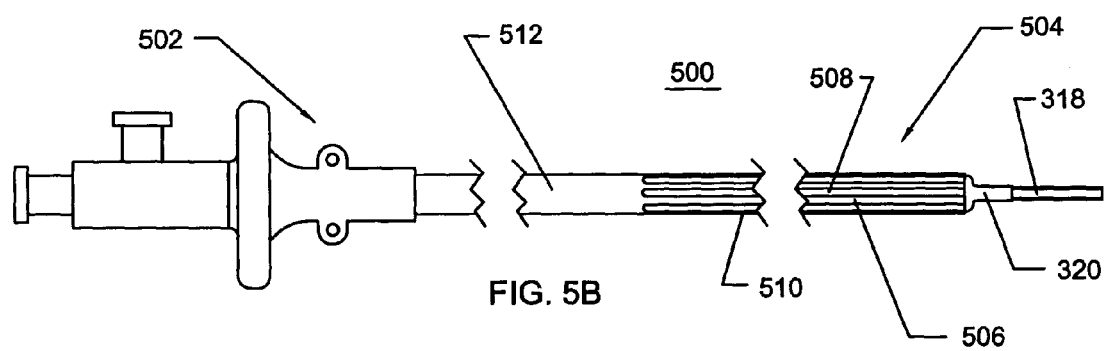
FIG. 5B illustrates a side view of the radially expandable sheath of FIG. 5A wherein the internal balloon dilator has expanded the distal portion of the sheath.

FIG. 5B illustrates the sheath 500 of FIG. 5A wherein the balloon 320 has dilated the distal section 504 diametrically. The proximal sheath cover 512 is unchanged but the longitudinal runners 506 or flutes 520 have moved apart circumferentially and the longitudinal slits or depressions 508 have become wider through unfolding or separating. The folded sheath tube 510 of the distal section 504 has become unfolded permanently or substantially permanently to an increased diameter. Because of reinforcements within the folded sheath tube 510, or because of internal strength and malleability or plastic deformation, the resultant distal section 504 is well supported in the open position by the folded sheath tubing 510 for subsequent instrument passage.

Figure 5C:
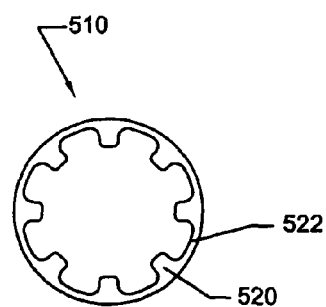
FIG. 5C illustrates a lateral cross-section of the distal portion of the transluminal sheath of FIG. 5A wherein the sheath covering comprises flutes or longitudinally disposed lines of increased thickness.

FIG. 5C illustrates a lateral cross-section of the distal end 504 of of the sheath 500. In this embodiment, the folded sheath tube 510 covering the distal section 504 is fabricated with flutes 520 on the interior, or exterior, surface. Interior flutes 520 are the preferred embodiment in this case. The flutes 520 represent longitudinally running increases in wall thickness, or high spots, of the folded sheath tube 510 which are separated by longitudinally running regions of decreased wall thickness 522 or depressions. The flutes 520 are generally integral to the folded sheath tube 510. The flutes 520 are generally created by fabricating an extrusion die with slots that permit the polymer to extrude with ridges thereon. The flutes 520 may facilitate folding and minimize damage to optical scopes, such as ureteroscopes, angioscopes, endoscopes, and the like, when inserted therethrough, due to debris scratching the lens when the scope is advanced or retracted. When the folded sheath tube 510 is dilated, the region of decreased wall thickness 522 between the flutes 520 will preferentially unfold because of the increased strength of the flutes 520.

FIG. 6A illustrates a side cutaway view of another embodiment of an expandable sheath 600 comprising a proximal sheath tube 602 and a distal sheath tube 604. The proximal sheath tube 602 further comprises a proximal reinforcing layer 612, an inner layer and an outer layer. The distal sheath tube 604 further comprises a longitudinal fold 606, a distal reinforcing layer 610, an outer layer 608, an inner layer 614, and a dilatation balloon 320. The sheath 600 also includes sheath and catheter hubs 308, 316 that can be arranged as described above.

Referring to FIG. 6A, in one embodiment, the proximal reinforcing layer 612 embedded within the proximal sheath tube 602, which is a composite structure, preferably formed from an inner and outer layer. The proximal reinforcing layer 612 can be a coil, braid, or other structure that provides hoop strength to the proximal sheath tube 602. The proximal reinforcing layer 612 can be fabricated from metals such as, but not limited to, stainless steel, titanium, nitinol, cobalt nickel alloys, gold, tantalum, platinum, platinum iridium, and the like. The proximal reinforcing layer 612 can also be fabricated from polymers such as, but not limited to, polyamide, polyester, and the like. Exemplary polymers include polyethylene naphthalate, polyethylene terephthalate, Kevlar, and the like. The proximal reinforcing layer 612, if it comprises metal, preferably uses metal that has been spring hardened and has a spring temper.

Further referring to FIG. 6A, the distal sheath tube 604 is constructed from a composite construction similar to that of the proximal sheath tube 602. The distal reinforcing structure 610, however, is preferably not elastomeric but is malleable. The distal reinforcing structure 610 is preferably a coil of flat wire embedded between the inner layer 614 and the outer layer 608. The crease or fold 606 runs longitudinally the length of the distal sheath tube 604 and is the structure that permits the distal sheath tube 604 to be compacted to a smaller diameter than its fully expanded configuration. There may be one fold 606, or a plurality of folds 606. The number of folds 606 can range between 1 and 20, and preferably between 1 and 8, with the sheath tubing 604 bendability and diameter having an influence on the optimal number of folds 606.

The construction of the distal sheath tube 604 can comprise a coil of wire with a wire diameter of 0.001 to 0.040 inches in diameter and preferably between 0.002 and 0.010 inches in diameter. The coil can also use a flat wire that is 0.001 to 0.010 inches in one dimension and 0.004 to 0.040 inches in the other dimension. Preferably, the flat wire is 0.001 to 0.005 inches in the small dimension, generally oriented in the radial direction of the coil, and 0.005 to 0.020 inches in width, oriented perpendicular to the radial direction of the coil. The outer layer 608 has a wall thickness of 0.001 to 0.020 inches and the inner layer 614 has a wall thickness of between 0.001 and 0.010 inches. The wire used to fabricate the coil can be fabricated from annealed materials such as, but not limited to, gold, stainless steel, titanium, tantalum, nickel-titanium alloy, cobalt nickel alloy, and the like. The wire is preferably fully annealed. The wires can also comprise polymers or non-metallic materials such as, but not limited to, PET, PEN, polyamide, polycarbonate, glass-filled polycarbonate, carbon fibers, or the like. The wires of the coil reinforcement can be advantageously coated with materials that have increased radiopacity to allow for improved visibility under fluoroscopy or X-ray visualization. The radiopaque coatings for the coil reinforcement may comprise gold, platinum, tantalum, platinum iridium, and the like. The mechanical properties of the coil are such that it is able to control the configuration of the fused inner layer 614 and the outer layer 608. When the reinforcing layer 610 is folded to form a small diameter, the polymeric layers, which can have some memory, do not generate significant or substantial springback. The sheath wall is preferably thin so that it any forces it imparts to the tubular structure are exceeded by those forces exerted by the malleable distal reinforcing layer. Thus, a peel away or protective sleeve is useful but not necessary to maintain the collapsed sheath configuration.

The inner layer 614 and the outer layer 608 preferably comprise some elasticity or malleability to maximize flexibility by stretching between the coil segments. Note that the pitch of the winding in the distal reinforcing layer 614 does not have to be the same as that for the winding in the proximal reinforcing layer 612 because they have different functionality in the sheath 600.

FIG. 6B illustrates a cutaway sectional view of the sheath 600 of FIG. 6A following expansion by the balloon 320. The proximal sheath tube 602 has not changed its diameter or configuration and the reinforcing layer 612 is likewise unchanged in configuration. The distal tube 604 has become expanded diametrically and the crease or fold 606 of FIG. 6A is now substantially removed. In the illustrated embodiment, due to stress hardening of the reinforcing layer and residual stress in the folded inner layer 614 and outer layer 608, some remnant of the fold 606 may still exist in the distal tube 604. The expansion of the sheath 600 in this configuration can be accomplished using a balloon 320 with an internal pressure ranging between 3 atmospheres and 25 atmospheres. Not only does the balloon 320 impart forces to expand the distal sheath tube 604 against the strength of the reinforcing layer 610 but it also should preferably overcome any inward radially directed forces created by the surrounding tissue. In an exemplary configuration, a sheath 600 using a flat wire coil reinforcing layer 610 fabricated from fully annealed stainless steel 304V and having dimensions of 0.0025 inches by 0.010 inches and having a coil pitch of 0.024 inches is able to fully expand, at a 37-degree Centigrade body temperature, to a diameter of 16 French with between 4 and 7 atmospheres pressurization. The inner layer 614 is polyethylene with a wall thickness of 0.003 to 0.005 inches and the outer layer 608 is polyethylene with a wall thickness of 0.005 to 0.008 inches. The sheath is now able to form a path of substantially uniform internal size all the way from the proximal end to the distal end and to the exterior environment of the sheath at both ends. Through this path, instrumentation may be passed, material withdrawn from a patient, or both. A sheath of this construction is capable of bending through an inside radius of 1.5 cm or smaller without kinking or becoming substantially oval in cross-section.

FIG. 7A illustrates a side view of another embodiment of an expandable sheath 700 comprising a proximal end 702 and a distal end 704. The sheath 700 further comprises an outer covering 706, a dilator shaft 708, a support frame 710, a dilatation balloon 712, a sheath hub 714, a dilator hub 716, a guidewire port 720, and a balloon inflation port 722. The distal end 704 has a reduced diameter relative to that of the proximal end 702.

Referring to FIG. 7A, the support frame 710 in the illustrated embodiment comprises a scaffold structure similar to a stent such as that used for treating stenoses in the coronary arteries. The support frame 710 is embedded within, or resides interior to and against, the inner diameter of the outer covering 706. The support frame may be fabricated from stainless steel, titanium, martensitic nitinol, gold, platinum, tantalum, or other materials commonly used to fabricate cardiovascular stents. The support frame may be fabricated from wire, it may be laser cut from a tube or sheet of metal, or it may be photo-etched, mechanically machined, or machined using electron discharge methodology. The support frame, in an embodiment, is malleable and remains in the state to which it is dilated by the dilatation balloon 712. The support frame is preferably radiopaque under the circumstances in which it is used in vivo and may be fabricated from, alloyed with, or coated with materials such as gold, platinum, platinum iridium, or tantalum. The support frame wall thickness can range from 0.002 to 0.025 inches and preferably be between 0.003 and 0.012 inches. The support frame preferably comprises structures that permit flexibility. Such flexibility enhancing structures include disconnected "Z" or diamond-shaped ring segments, ring segments connected by a backbone or alternating backbone of wire, continuous undulating spirals, and the like. The outer covering is either unfurling, malleably expansible, or elastomeric. An exemplary expansible outer covering 706 comprises a low-density polyethylene disposed so that it embeds the stent. Another expansible outer covering 706 comprises a polyurethane, silastic or thermoplastic elastomer sleeve disposed around and frictionally covering the support frame 710. The outer covering 706 may further comprise an inner layer that is relatively low in sliding friction such as, but not limited to, high density polyethylene, FEP, PTFE, or the like. A furled outer covering 706 may be fabricated from stretch blow-molded PET. The outer covering 706 may be coated on its interior, exterior, or both, by silicone slip agents, hydrophilic hydrogels, or the like to minimize friction in passing the catheter through the body lumen as well as passage of instruments therein.

FIG. 7B illustrates the sheath 700 of FIG. 7A wherein the support frame 710 has become expanded by the dilatation balloon 712 having been pressurized by fluid injected into the inflation port 722 on the dilator hub 716 and transmitted to the balloon 712 through the dilator shaft 708. The support frame 710, at the distal end 704, has malleably expanded and holds the outer covering 706 in its radially-expanded configuration.

Referring to FIG. 7B, the support frame 710 is affixed to the distal end of the proximal portion 702 of the sheath 700. The support frame 710 may be fully expanded at this proximal end even prior to expansion, as in FIG. 7A, and then neck down in the distal portion 704. Once expanded, the support frame 710 and the outer covering 706 have a generally continuous diameter and through lumen passing all the way from the proximal most portion of the sheath 700 to the distal end thereof. The outer covering 706 in the distal portion 704 will have stretched or unfurled to take on its larger diameter configuration. The recovery strength of the outer covering 706 is preferably such that it does not impart restorative forces greater than the resistive forces generated by the malleably expanded support frame 710. The distal region 704 remains dilated once the dilatation balloon 712, the dilator shaft 708, the dilator hub 716, and the inflation port 722 have all been removed from the sheath 700. Thus, a large central lumen is generated within the sheath 700.

FIG. 8A illustrates a side view of another embodiment of an expandable sheath 800 comprising a proximal region 802 and a distal region 808. In this embodiment, the proximal region 802 further comprises a braided reinforcement 804, a proximal sheath covering 806, and a proximal inner layer 832. The distal region 808 of this embodiment further comprises a distal sheath covering 810 and a distal reinforcement 812, and a distal inner layer 830. The distal region 808 has a reduced diameter relative to that of the proximal region 802 because the distal sheath covering 810 has been folded or furled to form one or more longitudinal creases or pleats 820. A transition region 822 connects the proximal sheath covering 806 and the distal sheath covering 810. Also shown is the dilator hub 316 and the guidewire access port 332.

Referring to FIG. 8A, the distal sheath region 808, which comprises the distal sheath covering 810, begins approximately at the transition region 822. The distal sheath covering 810 is thin-walled material that is folded into a plurality of pleats 820. The distal sheath covering 810 can be fused to a distal inner liner 830 and further cover or encompass a reinforcing layer 812. The distal sheath covering 810 is fabricated from materials such as, but not limited to, PET, polyethylene, polypropylene, Hytrel, Pebax, polyimide, polyamide, HDPE, and the like. The wall thickness of the distal sheath covering 810 ranges from 0.001 to 0.020 inches. The distal sheath covering 810 may be heat set, or cross-linked by irradiation (e.g. gamma radiation or electron beam radiation), to sustain the pleats, creases, or folds 820. The distal sheath covering 810 is affixed to the distal end of the proximal sheath covering 806 by welding or adhesive bonding. The proximal sheath covering 806 may be a unitary polymer tube fabricated from materials such as, but not limited to, Hytrel, Pebax, polyethylene, polyurethane, FEP, PTFE, or the like. The proximal sheath covering 806 may further be a composite reinforced structure with an internal coil or braid reinforcement 804 surrounded by polymers. The polymer on the proximal inner layer 832 may preferentially be a different polymer than that disposed on the exterior of the proximal sheath covering 806. Gamma radiation, electron beam radiation, proton irradiation, neutron irradiation, plasma discharge or the like may be used to modify the characteristics of the polymers used on the sheath, such as increasing their tensile strength, adhesiveness between layers, etc. The transition region 822 is designed to reduce or minimize stress risers that would occur if the proximal region 802 were butt-joined to the distal region 808. To optimize the transition 822, the proximal region 802 and the distal region 808 are feathered or serrated and the serrations interdigitated to generate a smooth segue between the mechanical properties of the proximal region 802 and the distal region 808. The serrations are preferably triangular in shape and between 0.10 and 5.00 centimeters long. The number of serrations can range between 1 and 20.

FIG. 8B illustrates an enlarged view of the distal tip of the distal region 808 of the sheath 800. The distal region 808 further comprises the distal sheath covering 810, the distal reinforcing layer 812, and the distal inner layer 830. The distal reinforcing layer 812, in this case a coil of malleable metal, further comprises a hoop end structure 834 and a weld 836. The distal region 808 further comprises an expandable radiopaque marker 838. The hoop end structure 834 is created by bring the final turn of the coil comprising the distal reinforcing layer 812 around and joining it to the prior coil using the weld 836. The weld 836 can also be an adhesive bond, crimp joint, or the like. The weld 836 is advantageously shaved or configured so as not to create a substantial bump, which could poke or project through the distal inner layer 830 or the distal sheath covering 810. The expandable radiopaque marker 838 can be comprised of malleable wire such as gold, tantalum, platinum, or the like. A plurality of turns of the wire, generally numbering between 1 and 20 turns, are sufficient to comprise a visible radiopaque marker 838. The radiopaque wire can be either flattened or round wire with a major dimension of between 0.001 inches and 0.020 inches. The wire is preferably foldable so that it can be creased longitudinally and collapsed diametrically along with the rest of the distal region 808. The multiple turn wire radiopaque marker 838 is advantageous, relative to other marker types because it embeds well in the polymer of the distal sheath covering 810 and offers less resistance to unfolding and expansion than would a band or solid ring.

Figure 9A:
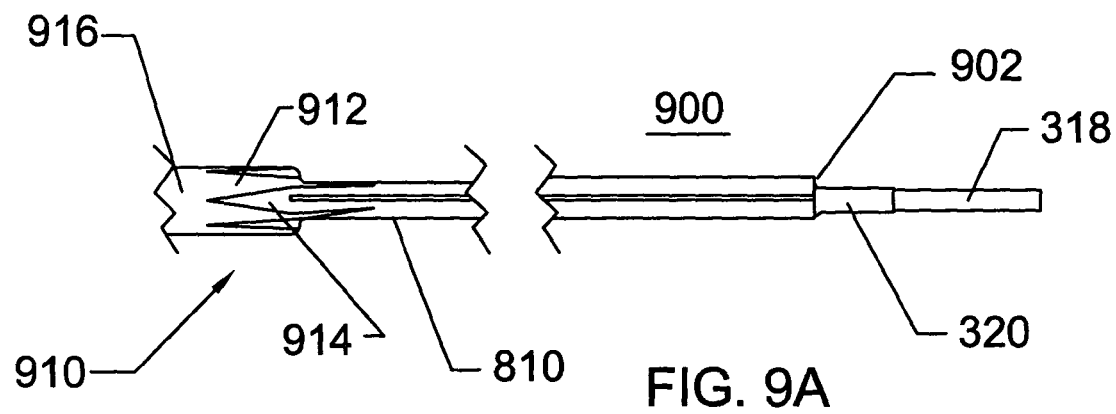
FIG. 9A illustrates the distal end of an embodiment of a radially expandable transluminal sheath with a step transition from the distal edge of the sheath and the balloon dilator.

FIG. 9A illustrates an embodiment of a collapsed, radially expandable sheath 900 comprising a large step transition 902 between the folded balloon 320 and the distal sheath covering 810. The sheath 900 further comprises a dilator shaft 318, to which the folded balloon 320 is affixed. Because of various folding configurations for the distal sheath covering 810, such step transitions 902 can occur. The step transitions 902, however, may catch on tissue as the sheath 900 is being advanced transluminally, thus impeding progress and potentially causing injury or trauma to the lumen wall. For example, referring to FIGS. 1 and 9A, during ureteral access procedures, the step transition 902 can catch on the tissues at the entrance 114 to the ureter 106 where the ureter 106 meets the bladder 104. Thus, in some embodiments, it is advantageous that a fairing be provided to minimize or eliminate the step transition 902. The sheath 900 further comprises a transition zone 910 between the distal sheath covering 810 and the proximal sheath covering 916, comprising distal chevrons 914 and proximal chevrons 912. The number of chevrons can vary between 2 and 30 with a preferred range of 4 to 16. The chevrons 912 and 914 can be welded, bonded, or fused and the tapered nature of the chevrons 912 and 914 enhances a smooth transition between the distal sheath covering 810 and the proximal sheath covering 916. In an embodiment, the distal sheath covering 810 and the proximal sheath covering 916 are fabricated from extruded polyolefin such as polyethylene. Reinforcements within the sheath coverings 810 and 916 can include coils, sleeves, tape, windings, braids, etc. and these are also transitioned within the chevrons 912 and 914 of the transition zone 910 or they are terminated outside the transition zone 910 so that no reinforcement exists within the transition zone 916. The chevrons 912 and 914 become distorted when the distal sheath covering 810 is folded or compressed longitudinally to its small diameter configuration. The dilator balloon (not shown) preferably extends proximally of the most proximal point of the transition zone 910.

Figure 9B:
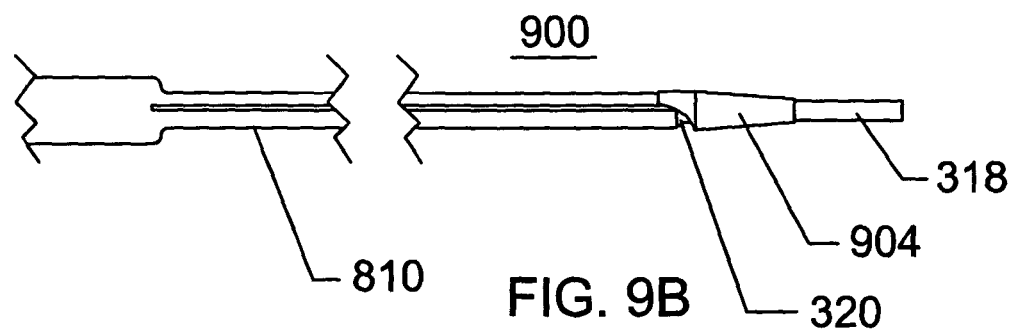
FIG. 9B illustrates the distal end of the radially expandable transluminal sheath of FIG. 9A wherein a fairing sleeve has been added to the dilator to smooth the step transition.

FIG. 9B illustrates a radially expandable sheath 900 comprising a fairing sleeve or distal shroud 904. In an embodiment, the distal shroud 904 is permanently affixed to the exterior of the dilator shaft 318 or the balloon 320 bond area. The distal shroud 904 may be rigid or it may be flexible or elastomeric. The distal shroud 904 covers the distal sheath covering 810 and holds the distal end of said covering 810 compressed against the dilator shaft 318 and the folded dilatation balloon 320. In another embodiment, the distal shroud 904 extends substantially to, but does not cover, the distal sheath covering 810 and serves as a nosecone for the distal sheath covering 810. In this embodiment, it is preferable that the gap between the proximal end of the distal shroud 904 and the distal end of the distal sheath covering 810 be minimized to prevent tissue from protruding therein. The distal shroud 904 may be fabricated from C-Flex, polyurethane, silicone elastomer, polyolefin, Hytrel, polyvinyl chloride, and the like. The distal shroud 904 can also be fabricated from bioresorbable or water dissolvable materials such as, but not limited to polylactic acid, polyglycolic acid, sugars, carbohydrates, or the like. Resorbable materials would be useful if the shroud 904 were to inadvertently come free from the dilator shaft 318 or balloon 320 and was left behind in the patient. The distal shroud 904 can further comprise radiopaque fillers such as, but not limited to, barium or bismuth salts, or tantalum powder. The distal shroud 904 can also comprise a radiopaque marker fabricated separately from platinum, gold, tantalum, iridium, or the like. The separate radiopaque marker can be insert molded, as in the case of a ring or band, or wound as in the case of wire, etc. The distal shroud 904 may be injection molded, liquid injection molded, thermally formed, or cut from an extrusion or dip-coated structure. The distal shroud 904 is preferably conical or tapered so that its diameter increases moving from the distal to the proximal direction. The distal shroud 904 may further be asymmetric or non-round in lateral cross-section to mate to the step transition 902, which may be larger in one circumferential location, than in another location. The distal shroud 904 generally has an undercut at its proximal end to allow the shroud to extend over the sheath covering 810, although it could also just butt up against the distal end of the sheath covering 810, without overlap. The distal shroud 904 is firmly bonded to the dilator shaft 318 or the balloon 320 so that it does not inadvertently come free from the sheath 900, a situation that could result in clinical complications. The bonding of the distal shroud 904 to the balloon 320 or the dilator shaft 318 may comprise heat welding, ultrasonic welding, adhesives, mechanical interlock, or a combination thereof. In an embodiment, the distal shroud 904 will deform and expand outward with the balloon 320, thus pulling away from the distal end of the distal sheath covering 810. When the distal sheath covering 810 has been expanded and the balloon 320 subsequently deflated, the distal shroud 904 will re-compress radially with the balloon 320 so that it can be withdrawn proximally through the internal lumen of the distal sheath covering 810.

The distal shroud 904 may further comprise an inner spacer (not shown) to prevent inadvertent withdrawal of the obturator or dilator, and shroud 904. A mechanism can be provided to allow the shroud to be advanced distally to release the sheath covering 810 so that it can expand. The inner spacer can further comprise, on its proximal end, a taper to facilitate proximal withdrawal into the sheath cover 810. The distal shroud 904 can be made thin and flexible so that it everts when the dilator is withdrawn proximally relative to the sheath covering 810. The inner spacer may further comprise an undercut or relief on its distal end, which allows the shroud to maintain a low profile, following eversion, prior to or during proximal withdrawal.

Figure 9C:
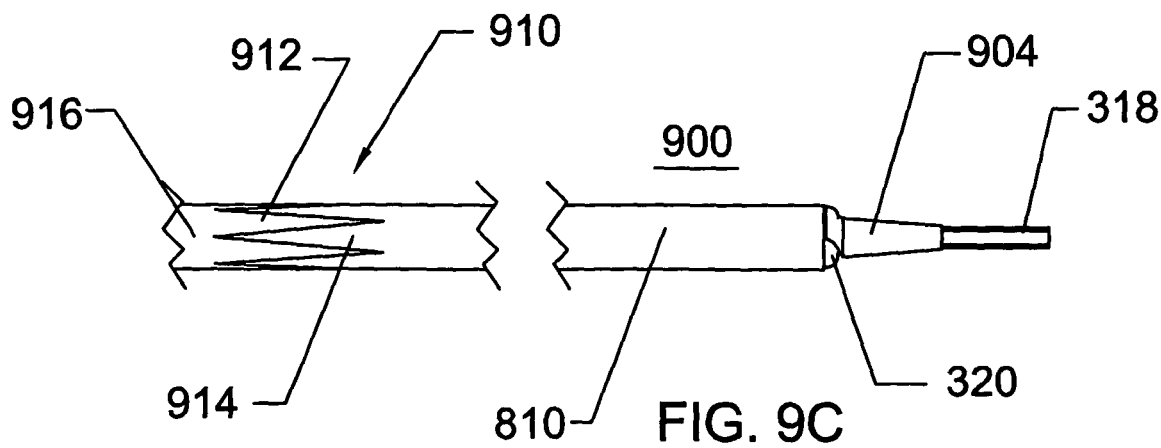
FIG. 9C illustrates the distal end of the radially expandable transluminal sheath of FIG. 9B, wherein the sheath has been expanded by a dilatation balloon, the fairing sleeve has slipped off the sheath distal edge and now resides against the outside of the dilatation balloon.

FIG. 9C illustrates the sheath 900 of FIG. 9B, following expansion, comprising a distal sheath covering 810, a proximal sheath covering 916, an expanded dilatation balloon 320, a dilator shaft 318, and a distal shroud 904. The sheath 900 further comprises the transition zone 910, the proximal chevron 912, and the distal chevron 914. The proximal part of the distal shroud 904 has been shown in breakaway fashion to reveal the balloon 320. The proximal end of the distal shroud 904 has expanded elastomerically with the balloon 320 and, in so doing, has retracted distally from covering or overlapping the distal end of the distal sheath covering 810. Attachment of the distal end of the distal shroud 904 to the balloon 320 or the dilator shaft 318 prevents motion of the distal end of the distal shroud 904 in the proximal direction. Following the next step, which is deflation of the balloon 320, the elastomeric distal shroud 904 will reduce in diameter and be able to be withdrawn through the central lumen of the distal sheath tube whose outer layer is the covering 810. The transition zone 910 has expanded and become substantially of constant diameter since the distal sheath covering 810 has been radially expanded. The proximal chevrons 914 and the distal chevrons 912, which are interdigitated and affixed by fusing, gluing, bonding, welding, sleeving, or clamping together, are generally undistorted and form a substantially even zig-zag pattern with a substantially smooth gradual transition in properties when going from the proximal sheath tubing 916 to the distal sheath covering 810. The transition zone 910 thus comprises a plurality of tapered, interdigitated chevrons 912 and 914 of the proximal region and the distal region, said regions being at least partially affixed together along the edges of the chevrons 912 and 914.

In another embodiment, the distal end of the distal sheath covering 810 comprises extra material (not shown) that extends distally toward the exposed dilator shaft 318. This extra material can be symmetrically disposed around the circumference of the distal sheath covering 810 or it can be asymmetrically distributed so as to form a canopy that extends only over half of the sheath distal end. Following folding, the canopy can be further heat set or formed to form a fairing to minimize or eliminate the step transition 902. While the coil or braid reinforcement can also support the transition canopy, it is preferable that any internal reinforcement not extend into the canopy or distal sheath covering extension. In an embodiment where the reinforcing layer is a braided structure, a pick count ranging between 10 and 30 picks per inch and between 8 and 42 carriers of strand is appropriate for this application.

Referring to FIGS. 3A, 8A, and 9A, in an embodiment, the dilator shaft 318 can comprise a central through lumen 334, generally 0.010 to 0.060 inches in diameter that is operably connected to the guidewire port 332 on the dilator hub 316. The dilator shaft 318 is affixed to the dilator hub 316 by insert molding, welding, adhesive bonding, or the like. The dilator hub 316 can be advanced forward causing the dilator shaft 318 to advance relative to the distal sheath covering 810. The shroud 904 pulls forward therewith and no longer surrounds the exterior of the distal sheath covering 810. The sheath covering 810 is now free to expand by unfurling the pleats or folds 820 and serve as potential space for instrumentation once the obturator shaft 318 and its associated components are withdrawn from the sheath 900. In another embodiment, the shroud 904 is evertable and the dilator hub 316 is withdrawn proximally to simply pull the shroud 904 off the sheath covering 810 and out through the central lumen of the sheath 900. The shroud 904, in this embodiment, may be fabricated from metals such as stainless steel or from polymers such as C-Flex, polypropylene, polyethylene, polyurethane, silicone elastomer, and the like.

FIG. 10A illustrates a lateral cross-section of an embodiment of the distal tubing 1008, which can be used in combination with the sheath embodiments described above. The distal tubing, in this embodiment, is extruded or formed with thin areas 1032 and normal wall 1030. The illustrated embodiment shows two thin areas 1032 prior to folding. The spacing and magnitude of the thick and thin areas do not necessarily have to be uniformly placed or equally sized. The thin areas can be used to enhance the ability to form tight folds for diameter reduction.

FIG. 10B illustrates the distal tubing 1008 of FIG. 10B after it has been folded longitudinally. Other folds, including Napster™-type styles, star shapes, clover-leafs, folded "W"s, and the like, are also possible. Such profiling can be performed on tubing fabricated from materials such as, but not limited to, polyethylene, PTFE, polyurethane, polyimide, polyamide, polypropylene, FEP, Pebax, Hytrel, and the like, at the time of extrusion. The distal tubing 1008 would then be used, as-is, or it would be built up onto a mandrel with other layers as part of a composite tube. The composite tube can include coil, braid, or stent reinforcement. The thin areas 1032 facilitate tight folding of the layer 1008 and minimize the buildup of stresses and strains in the material that might prevent it from fully recovering to a round shape following unfolding.

FIG. 10C illustrates a lateral cross section of the distal end of the sheath 600 of FIG. 6A. In the illustrated embodiment, the balloon 320 has been folded to form four longitudinal creases, furls, or pleats 1020. The dilator shaft 318 remains in place in the center of the balloon 320 and is fluidically sealed to the balloon 320 at the distal end of said balloon 320. The compressed sheath covering 1008 surrounds the folded balloon 320. When the balloon 320 is expanded under pressure from an external pressure source, the balloon expands the sheath covering 1008 to a larger diameter. The sheath covering 1008 maintains that configuration held in place by the malleable sheath reinforcement or by the malleable nature of the unitary sheath covering 1008, should a separate reinforcement not be used.

FIG. 10D illustrates a lateral cross-section of an embodiment of a sheath tube comprising an inner layer 1052, a reinforcing layer 1056, an elastomeric layer 1054, and an outer layer 1050. The elastomeric layer 1054 can be disposed outside the reinforcing layer 1056, inside the reinforcing layer 1056, or both inside and outside the reinforcing layer 1056. The elastomeric layer 1054 is fabricated from silicone elastomer, thermoplastic elastomer such as C-Flex™, a trademark of Concept Polymers, polyurethane, or the like. The hardness of the elastomeric layer 1054 can range from Shore 10A to Shore 90A with a preferred range of Shore 50A to Shore 70A. The inner layer 1052 and the outer layer 1050 are fabricated from lubricious materials such as, but not limited to, polyethylene, polypropylene, polytetrafluoroethylene, FEP, materials as described in FIG. 8A, or the like. The inner layer 1052 and the outer layer 1050 can have a thickness ranging from 0.0005 inches to 0.015 inches with a preferred range of 0.001 to 0.010 inches. The elastomeric layer 1054 can range in thickness from 0.001 inches to 0.015 inches with a preferred range of 0.002 to 0.010 inches. The reinforcing layer 1056 is as described FIG. 6A. This construction is beneficial for both the proximal non-expandable region and the distal expandable region of the sheath. In an embodiment, the C-Flex thermoplastic elastomer is used for the elastomeric layer 1054 because it fuses well to the polyethylene exterior layer 1050. This embodiment provides for improved kink resistance, improved bendability, and reduced roughness or bumpiness on the surface of the sheath where the elastomeric layer 1054 shields the reinforcing layer 1056. This embodiment provides for a very smooth surface, which is beneficial on both the interior and exterior surfaces of the sheath.

FIG. 10E illustrates a lateral cross-sectional view of an embodiment of an expandable sheath distal section 1040. The sheath distal section 1040 comprises a dilator tube 318, a dilator balloon, 320, and an outer sheath covering 1042, further comprising a first fold 1044 and a second fold 1046. For sheaths with a wall 1042 thickness of about 0.008 to 0.020, it is useful to fold the sheath covering 1042 into two folds 1044 and 1046 if the inside diameter of the expanded sheath ranges greater than 12 French. If the inside diameter of the expanded sheath covering 1042 is less than about 12 French, and sometimes when the sheath covering 1042 is substantially equal to 12 French, it is preferred to have only a single fold, either 1044 or 1046. If the diameter of the sheath covering 1042 is greater than 18 French, or the wall thickness of the sheath covering 1042 is less than the range of about 0.008 to 0.020 inches, or both, additional folds can be added.

FIG. 11A illustrates a side view of another embodiment of an expandable sheath 1100 comprising a proximal end 1102 and a distal end 1104. The sheath 1100 further comprises an outer covering 1106, a dilator shaft 1108, a split-ring support frame 1110, a dilatation balloon 1112, a sheath hub 1114, a dilator hub 1116, a guidewire port 1120, and a balloon inflation port 1122. The distal end 1104 has a reduced diameter relative to that of the proximal end 1102.

Referring to FIG. 11A, the split-ring support frame 1110 is a malleable structure that can be dilated by forces exerted by the inflated balloon 1112. The dilation is the same as that generated by the sheath 700 of FIGS. 7A and 7B. The split-ring support frame can be fabricated from wire or from flat sheets of metal, from wires, or from tubes of metal. The preferred metal is selected from materials such as, but not limited to, cobalt nickel alloys, titanium, tantalum, annealed stainless steels such as 316L, 304, and the like. The split ring support frame 1110 is disposed inside the inner diameter of the distal sheath tubing 1106. The split ring support frame 1110 has the advantage of being inexpensive to fabricate relative to other stent-like support designs. The split ring support frame 1110 can be configured as a series of ribs and a backbone, or as a series of staggered backbones to facilitate flexibility along more than one axis. Alternatively, in another embodiment, the split ring support frame 1110 can be self-expanding. The preferred configuration for the distal sleeve 1106 is a thin wall polymer that is furled into longitudinal flutes. The split ring can comprise rings whose ends overlap circumferentially when the sheath is collapsed diametrically, as well as being expanded diametrically. Furthermore, the split ring configuration can comprise rings that do not overlap in the collapsed configuration, the expanded configuration, or both.

FIG. 11B illustrates the sheath 1100 of FIG. 11A wherein the support frame 1110 has become expanded by the dilatation balloon 1112 having been pressurized by fluid injected into the inflation port 1122 on the dilator hub 1116 and transmitted to the balloon 1112 through the annulus between the outer and inner tubes comprising the dilator shaft 1108. The split-ring support frame 1110, at the distal end 1104, has malleably expanded and holds the outer covering 1106 in its radially expanded configuration. The through lumen of the distal end 1104 is substantially similar to that of the proximal end 1102.

Figure 12:
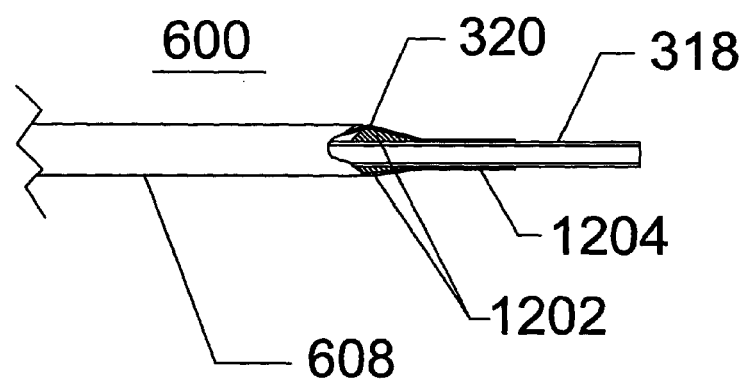
FIG. 12 illustrates the distal end of an embodiment of a radially expandable sheath with a fairing internal to the balloon.

FIG. 12 illustrates another embodiment of the catheter 600, wherein the step transition 902 of FIG. 9A can be minimized by the inclusion of a gel, foam, or liquid-filled sac 1202 within balloon 320 just proximal to the distal balloon bond 1204, which is the region where the balloon 320 is bonded to the dilator shaft 318. When the distal sheath covering 608 and the balloon 320 are folded and collapsed, the material within the sac 1202 will remain puffed out and create a fairing within the balloon that smoothes the transition 902. A key advantage of such an internal fairing is that it cannot become dislodged from the sheath 600. The sac 1202 can be free-form, it can be circular in cross-section, or it can be non-circular and oriented to conform to circumferential irregularities in the transition 902. In another embodiment, the sac 1202 is filled with a resilient polymer following assembly of the collapsed sheath to the folded dilator so that a custom fairing 1202 is created. In yet another embodiment, there is no sac, but an internal fairing 1202 is created using a foam, or a low durometer polymer. This internal fairing 1202 is located on the distal dilator shaft 318 inside the balloon 320. This embodiment can further comprise a coating of lubricious material such as silicone elastomer, hydrogel, or the like, on the inside of the sheath tubing 608 or the outside of the balloon 320 to aid in sliding the balloon with internal fairing proximally out of the sheath tubing 608.

Referring to FIG. 12, in another embodiment, once the sheath tubing 608 is collapsed around the balloon 320, the balloon 320 is filled at its distal end by way of a special filling tube (not shown) that is either integral to, or separate from, the dilator shaft 318. The distal end of the balloon 320, in this embodiment, is shaped using an external mold (not shown) during filling. The materials used to fill the balloon 320 distal end include, but are not limited to, hardenable liquid polymers, gel, and foam that is injected in a liquid state and then hardens or sets up. The filling tube is removed or closed off and the resin is allowed to set-up, or harden, in the shape of the external mold. The filled distal end of the balloon 320 forms a tapered fairing 1202 that minimizes or eliminates any transitions between the sheath and the balloon. In another embodiment, an external mold is not used but the filling is performed under visual inspection and correction to generate the correct shape.

In another embodiment, the dilator shaft 318 is formed with a tailored bump 1202 that is positioned just proximal to the distal balloon 320 to dilator shaft 318 bond. The bump 1202 is configured to form a taper and fairing under the distal shoulder of the balloon 320 that ramps up to meet the sheath tubing 608 and minimize or eliminate any transition shoulder. Since a coaxial annulus is used to fill the balloon 320, the proximal balloon bond (not shown) is larger in diameter than the distal balloon bond 1204 and the proximal balloon bond can be slid over the bump allowing the bump to reside within the balloon 320. The bump 1202 is created by a thermoforming process either free form, or preferably using a mold, internal pressure, and the like. The dilator shaft 318, under the bump 1202 in this embodiment, may be thinned or formed into a bulb to create the bump 1202.

FIG. 13A illustrates an embodiment of the proximal end of a radially expandable sheath 1300 for endovascular use further comprising a valve 1302 operably connected to the sheath hub 1304 and a hemostatic valve 1306 operably connected to the dilator hub 1308. In this embodiment, the valve 1302 is a duckbill valve, one-way valve, or other sealing-type valve capable of opening to a large bore and yet closing around instrumentation such as the dilator shaft 1320. The valve 1302 seals against fluid loss from the internal lumen of the sheath 1300 while the dilator hub 1308 is connected to the sheath hub 1304 and after the dilator shaft 1320 has been removed from the sheath 1300. The valve 1302 can be integral to the sheath hub 1304, it can be welded or adhered to the sheath hub 1304, or it can be affixed by a Luer fitting or other quick connect fitting. The hemostatic valve 1306 is a Tuohy-Borst valve or other valve capable of sealing against a guidewire or small instrument and remain sealed after removal of said guidewire or small instrument. The hemostatic valve 1306 may further comprise a tightening mechanism (not shown) to enhance sealing against guidewires or against an open lumen. The hemostatic valve 1306 can be integral to the dilator hub 1308, it can be welded or adhered to the dilator hub 1308, or it can be affixed by a Luer fitting or other quick connect fitting. The valves 1306 and 1302 are generally fabricated from polymeric materials and have soft resilient seal elements disposed therein. The hemostatic valve 1306 is intended to minimize or prevent blood loss from vessels at systemic arterial pressure for extended periods of time. The valve 1302 is intended to minimize or eliminate blood loss when instrumentation of various diameters is inserted therethrough.

FIG. 13B illustrates an embodiment of the proximal end of a radially expandable sheath 1310 for laparoscopic use, further comprising a valve 1312 operably connected to the sheath hub 1314. The valve 1312 is intended primarily to prevent or minimize the loss of fluids (liquids or gasses) from an abdominal or thoracic cavity. The valve 1312 is generally fabricated from polymeric materials and has soft resilient seal elements disposed therein. The valve 1312 can be integral to the sheath hub 1314, it can be welded or adhered to the sheath hub 1314, or it can be affixed by a Luer fitting or other quick connect fitting. The dilator hub 1308 is also shown.

Figure 14:
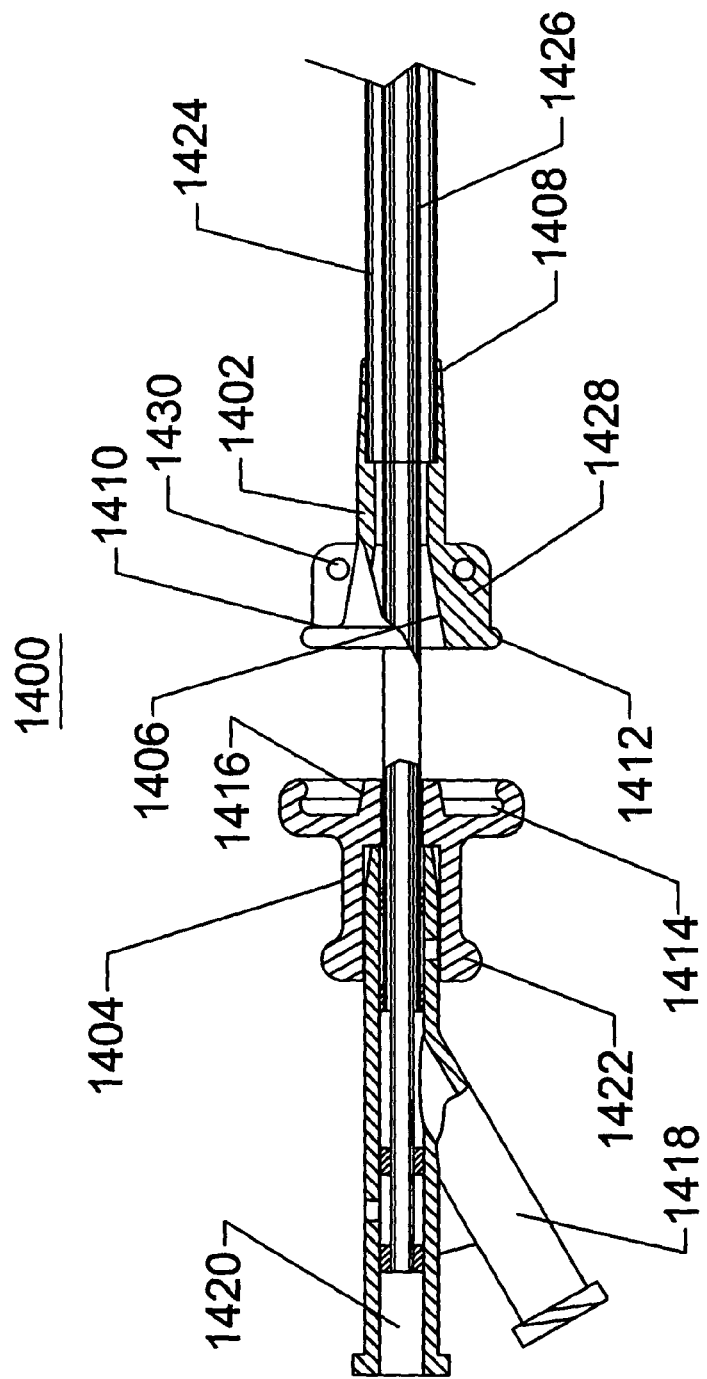
FIG. 14 illustrates a cross-sectional view of the proximal end of a another embodiment of a radially expandable sheath hub and dilator hub.

FIG. 14 illustrates a longitudinal cross-sectional view of the proximal end of an embodiment of an expandable sheath system 1400. The expandable sheath system 1400 comprises a sheath hub 1402, a dilator hub 1404, a sheath tube 1424 and a dilator tube 1426. The sheath hub 1402 further comprises a proximal port 1406, a distal end 1408, a distal face 1410, and a proximal perimeter 1412. The dilator hub 1404 further comprises an engagement detent 1414, a distal taper 1416, a grip handle 1422, an inflation port 1418, and a guidewire port 1420. The sheath hub 1402 can optionally comprise one or more fins 1428 which can further comprise one or more attachment holes or slots 1430.

Referring to FIG. 14, the distal face 1410 is oriented substantially perpendicularly to the axis of the sheath tube 1424, but it could also be at an angle. The distal face 1410 can have a small round or fillet structure to eliminate any sharp corners where it interfaces to the more cylindrical regions of the sheath hub 1402. The proximal perimeter 1412, in this embodiment, is configured to mate with the engagement detent 1414 in the dilator hub 1404, which has a slight undercut and a tapered lead in. The proximal perimeter 1412 can be a continuous band surrounding up to 360 degrees of the circumference of the sheath hub 1402. The proximal perimeter 1412 is preferably rounded or chamfered to ease connection and disconnection with the dilator hub 1404 and its engagement detent 1414. The sheath hub 1402 and the dilator hub 1404 can be fabricated from polymers such as, but not limited to ABS, polysulfone, PVC, polyolefin including polyethylene or polypropylene, polyamide, polycarbonate, and the like. In a preferred embodiment, the sheath hub 1402 and the dilator hub 1404 are fabricated from different polymers to minimize the risk of blocking.

Referring to FIG. 14, the distal end 1408 of the sheath hub 1402 is tapered to an increasingly small diameter moving distally so that the distal end 1408, as well as the proximal end of the sheath tube 1424, can slip substantially within a body vessel or lumen, for example a urethra. The proximal port 1406 of the sheath hub 1402 can be straight, it can be tapered, or it can have a straight taper to facilitate sealing with the dilator distal taper 1416. The taper angle can be between 1 degree and 20 degrees on each side. The dilator hub knob 1422 is integral to the dilator hub 1404 and provides an enlargement that can be gripped by the user to facilitate separation of the dilator hub 1404 from the sheath hub 1402. The dilator hub knob 1422 also can be used between the thumb and a finger or between two fingers to advance the entire assembly or remove the assembly from the patient.

The present invention may be embodied in other specific forms without departing from its spirit or essential characteristics. For example, the sheath may include instruments affixed integrally to the interior central lumen of the mesh, rather than being separately inserted, for performing therapeutic or diagnostic functions. The hub may comprise tie downs or configuration changes to permit attaching the hub to the skin of the patient. The embodiments described herein further are suitable for fabricating very small diameter catheters, microcatheters, or sheaths suitable for cardiovascular or neurovascular access. These devices may have collapsed diameters less than 3 French (1 mm) and expanded diameters of 4 to 8 French. Larger devices with collapsed diameters of 16 French and expanded diameters of 60 French or larger are also possible. Such large devices may have orthopedic or spinal access applications, for example. The described embodiments are to be considered in all respects only as illustrative and not restrictive.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An expandable transluminal access sheath adapted for providing minimally invasive access to body lumens or cavities, comprising:
an axially elongate sheath tube with a proximal end and a distal end and a central through lumen;
a distal region of the sheath tube which is expandable in circumference in response to pressure applied therein, the distal region being folded along one or more longitudinal creases to a diameter smaller than that of the proximal end of the elongate sheath tube and having a composite structure comprising a malleable reinforcement embedded within an outer layer and an inner layer, the malleable reinforcement being folded and holding the distal region in its folded, smaller diameter configuration by overcoming forces imparted by the sheath tube;
a hub affixed to the proximal end of the sheath tube, the hub adapted to form a tapered internal lumen to facilitate the passage of instrumentation;
a central obturator, which serves to occlude the central lumen of the sheath during insertion; and
a guidewire lumen within the obturator, capable of passing standard medical guidewires;
wherein the obturator is a balloon dilator and radial expansion of the balloon dilator causes the distal region, including the malleable reinforcement, to expand diametrically to an expanded configuration, with the malleable reinforcement maintaining the distal region in its expanded configuration.

2. The transluminal sheath of claim 1 wherein the outer layer and the inner layer comprise a polymer.

3. The transluminal sheath of claim 2 wherein the sheath bends predominantly by plastic deformation rather than elastic deformation.

4. The transluminal sheath of claim 2 wherein the sheath bends predominantly by plastic deformation, said deformation being enhanced by subjecting the sheath to temperatures substantially near those of body temperature.

5. The transluminal sheath of claim 2 wherein the malleable reinforcement is a braided structure fabricated from polymeric materials.

6. The transluminal sheath of claim 2 wherein the malleable reinforcement is substantially deformable in cross-section.

7. The transluminal sheath of claim 2 wherein the sheath tube is substantially deformable in cross-section in response to irregularly shaped objects being advanced or withdrawn therethrough.

8. The transluminal sheath of claim 2 wherein the sheath comprises a radiopaque marker.

9. The sheath of claim 2 wherein the inner surface of the inner layer of the sheath comprises longitudinally running flutes for reducing friction between the inner layer and instrumentation or material being advanced or withdrawn therethrough.

10. The sheath of claim 2 wherein the inner surface of the inner layer is dimpled to enhance liquid surface coating of said liner.

11. The sheath of claim 2 wherein the outer surface of the outer layer comprises longitudinally oriented ridges and adjacent valleys, the purpose of which is to enhance liquid transmission along the outer surface of said sheath.

12. The sheath of claim 2 wherein the malleable reinforcement comprises a coil, wherein the coil is welded or fused to itself at the distal end of the sheath so as to form a ring structure.

13. The sheath of claim 2 wherein the malleable reinforcement comprises a coil, wherein the coil is wound onto the inner layer of the sheath with substantially neutral spring tension.

14. The transluminal sheath of claim 1 wherein the balloon dilator comprises a central guidewire lumen.

15. The obturator of claim 1 further comprising a tapered tip further comprising multiple tapers and diameters.

16. The obturator of claim 1 comprising a tapered tip which is substantially cylindrical at the distal end, tapering up to a larger cylinder at its proximal end.

17. The obturator of claim 1 wherein a distal end of a tapered tip is capable of tracking over a 0.035 to 0.038-inch diameter guidewire around corners as tight as 1.5-cm radius.

18. The obturator of claim 1 wherein the distal tip of the dilator is no larger than 4.5 French in diameter.

19. The obturator of claim 1 wherein the outer surface of said obturator comprises longitudinally oriented ridges and adjacent valleys, the purpose of the ridges and valleys being to minimize friction between the obturator and the inner surface of the sheath.

20. The sheath of claim 1 further comprising a cap hub on the obturator that securely and reversibly fastens to the hub on the sheath and locks in two substantially orthogonal axes.

21. The sheath of claim 1 wherein the inner surface of the sheath comprises longitudinally running ridges and adjacent valleys.

22. The sheath of claim 1 further comprising an atraumatic tip.

23. The sheath of claim 1 further comprising a sheath tube tip fabricated from materials softer than those used on the sheath tube.

24. The sheath of claim 1 wherein a proximal region of the sheath tube is non-expandable.

* * * * *